(12) United States Patent
Berbeco et al.

(10) Patent No.: US 11,590,225 B2
(45) Date of Patent: Feb. 28, 2023

(54) BISMUTH-GADOLINIUM NANOPARTICLES

(71) Applicants: The Brigham and Women's Hospital, Inc., Boston, MA (US); UNIVERSITÉ CLAUDE BERNARD LYON 1, Villeurbanne (FR); NH THERAGUIX, Villeurbanne (FR); CENTRE NATIONAL DE LA RECHERCHE SCIENTIFIQUE, Paris (FR)

(72) Inventors: Ross Berbeco, Cambridge, MA (US); Eloise Thomas, Montmorillon (FR); Francois Lux, Lyons (FR); Olivier Tillement, Fontaines Saint Martin (FR); Alexandre Detappe, Boston, MA (US); Geraldine Le Duc, Crolles (FR)

(73) Assignees: The Brigham and Women's Hospital, Inc., Boston, MA (US); NH TherAguix, Villeurbanne (FR); Université Claude Bernard Lyon 1, Villeurbanne (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 16/467,698

(22) PCT Filed: Dec. 8, 2017

(86) PCT No.: PCT/US2017/065365
§ 371 (c)(1),
(2) Date: Jun. 7, 2019

(87) PCT Pub. No.: WO2018/107057
PCT Pub. Date: Jun. 14, 2018

(65) Prior Publication Data
US 2020/0000915 A1 Jan. 2, 2020

Related U.S. Application Data

(60) Provisional application No. 62/431,607, filed on Dec. 8, 2016.

(51) Int. Cl.
| A61K 41/00 | (2020.01) |
| A61P 35/00 | (2006.01) |
| A61K 9/00 | (2006.01) |
| A61K 9/51 | (2006.01) |
| A61K 49/04 | (2006.01) |
| A61K 49/10 | (2006.01) |
| A61K 49/18 | (2006.01) |
| A61N 5/10 | (2006.01) |

(52) U.S. Cl.
CPC ........ *A61K 41/0038* (2013.01); *A61K 9/0019* (2013.01); *A61K 9/0043* (2013.01); *A61K 9/5115* (2013.01); *A61K 9/5146* (2013.01); *A61K 49/049* (2013.01); *A61K 49/108* (2013.01); *A61K 49/1824* (2013.01); *A61N 5/10* (2013.01); *A61P 35/00* (2018.01); *A61N 2005/1098* (2013.01)

(58) Field of Classification Search
CPC ............ A61K 41/0038; A61K 49/1824; A61K 49/108; A61K 9/5115; A61K 9/0019; A61K 9/0043; A61K 49/049; A61K 9/5146; A61P 35/00; A61N 5/10; A61N 2005/1098
See application file for complete search history.

(56) References Cited

U.S. PATENT DOCUMENTS

| 5,208,324 A | 5/1993 | Klaveness et al. |
| 2003/0180780 A1 | 9/2003 | Feng et al. |
| 2007/0275383 A1 | 11/2007 | Vocanson et al. |
| 2012/0076737 A1 | 3/2012 | Chen et al. |
| 2014/0276021 A1 | 9/2014 | Yeh et al. |
| 2015/0050217 A1 | 2/2015 | Cremillieux et al. |
| 2016/0115187 A1 | 4/2016 | Tripier et al. |
| 2020/0197540 A1* | 6/2020 | Negussie ............. A61K 9/1635 |

FOREIGN PATENT DOCUMENTS

| CN | 1378083 | 12/2005 | |
| CN | 102327625 | 1/2012 | |
| CN | 102757786 | * 10/2012 | ........... A61B 5/1172 |
| FR | 2863053 | 6/2005 | |
| FR | 2867180 | 9/2005 | |
| FR | 2922106 | 4/2009 | |
| FR | 2989280 | 10/2013 | |
| WO | WO 03080743 | 10/2003 | |
| WO | WO 2005120590 | 12/2005 | |
| WO | WO 2006012201 | 2/2006 | |
| WO | WO 2011135101 | 11/2011 | |

OTHER PUBLICATIONS

Guo et al., J. Phys. Chem. C, 2010, 114, 49, p. 21390-21396. (Year: 2010).*
https://en.wikipedia.org/wiki/Ligand, Jun. 6, 2021. (Year: 2021).*
Titus et al., Appl. Microbiol Biotechnol, 2016, 100, p. 4803-16. (Year: 2016).*
Bryant et al., "Synthesis and relaxometry of high-generation (G = 5, 7, 9, and 10) PAMAM dendrimer-DOTA-gadolinium chelates," Journal of Magnetic Resonance Imaging, Feb. 1999, 9(2):348-352.
EP Extended European Search Report in European Appln. No. 17878113, dated Jul. 10, 2020, 11 pages.
Fang et al., "Dendrimer-stabilized bismuth sulfide nanoparticles: synthesis, characterization, and potential computed tomography imaging applications," Analyst, Mar. 2013, 138(11):3172-3180.
Alqathami et al., "Quantitative 3D determination of radiosensitization by bismuth-based nanoparticles," Journal of Biomedical Nanotechnology, Mar. 1, 2016, 12(3):464-71.

(Continued)

*Primary Examiner* — Michael G. Hartley
*Assistant Examiner* — Leah H Schlientz
(74) *Attorney, Agent, or Firm* — Fish & Richardson P.C.

(57) ABSTRACT

Provided herein are nanoparticle compositions (e.g., nanoparticle compositions comprising high atomic number ions) that are useful for imaging diseases in a subject as well as radiosensitizing a disease in a subject (e.g., radiosensitizing a cancer in the subject). Methods of imaging a subject, methods of treating cancer, and processes of preparing the nanoparticle compositions are also provided.

9 Claims, 17 Drawing Sheets

(56) References Cited

OTHER PUBLICATIONS

Aviv et al., "Synthesis and characterization of Bi2O3/HSA core-shell nanoparticles for X-ray imaging applications," Journal of Biomedical Materials Research Part B: Applied Biomaterials., Jan. 2013, 101(1):131-8.

Barnett et al., "Normal tissue reactions to radiotherapy: towards tailoring treatment dose by genotype," Nature Review, Feb. 2009, 9(2):134-142.

Bazzi et al., "Synthesis and luminescent properties of sub-5-nm lanthanide oxides nanoparticles," Journal of Luminescence, May 1, 2003, 102:445-50.

Bissonnette et al., "Cone-beam computed tomographic image guidance for lung cancer radiation therapy," Int. J. Radiat. Oncol. Biol. Phys., Mar. 2009, 73(3):927-934.

Bridot et al., "Hybrid gadolinium oxide nanoparticles: multimodal contrast agents for in vivo imaging," Journal of the American Chemical Society, Apr. 25, 2007, 129(16):5076-84.

Brower et al., "Improved survival with dose-escalated radiotherapy in stage III non-small-cell lung cancer: analysis of the National Cancer Database," Ann. Oncol., Aug. 2016, 27(1):1887-1894, 26 pages.

Cannas et al., "Synthesis, characterization and optical spectroscopy of a Y2O3—SiO2 nanocomposite doped with Eu3+," Journal of Non-Crystalline Solids, Aug. 1, 2002, 306(2):193-9.

Carpenter et al., "CellProfiler: image analysis software for identifying and quantifying cell phenotypes," Genome Biology, Apr. 2006, 7(10):R100, 11 Pages.

Choi et al., "Renal clearance of quantum dots," Nature Biotechnology, Oct. 2007, 25(10):1165-70.

Csajbók et al., "Equilibrium, 1H and 13C NMR spectroscopy, and X-ray diffraction studies on the complexes Bi (DOTA)-and Bi (DO3A-Bu)," Inorganic Chemistry, Apr. 7, 2003, 42(7):2342-9.

Daniel et al, "Gold nanoparticles: assembly, supramolecular chemistry, quantum-size-related properties, and applications toward biology, catalysis, and nanotechnology," Chemical Reviews, Jan. 14, 2004, 104(1):293-346.

Dawson et al., "Advances in image-guided radiation therapy," Journal of Clinical Oncology: Official Journal of the American Society of Clinical Oncology, Mar. 2007, 25:938-946.

Dawson et al., "Imaging in Radiation Oncology: A Perspective," Oncologist, Apr. 2010, 15(4):338-349.

De Ruysscher., "Radical treatment of synchronous oligometastases from NSCLC," Lancet Oncol., Oct. 2016, 17(12):1625-1626.

Detappe et al., "Advanced multimodal nanoparticles delay tumor progression with clinical radiation therapy," Journal of Controlled Release, Sep. 28, 2016, 238:103-13.

Detappe et al., "AGuIX nanoparticles as a promising platform for image-guided radiation therapy," Cancer Nanotechnology, Dec. 2015, 6(1):4, 9 Pages.

Feng et al., "Functionalized europium oxide nanoparticles used as a fluorescent label in an immunoassay for atrazine," Analytical Chemistiy, Oct. 1, 2003, 75(19):5282-6.

French Preliminary Research Report for Appln. No. 0402115, dated Oct. 13, 2004, 3 pages.

French Preliminary Research Report for Appln. No. 0758348, dated Mar. 12, 2008, 2 pages.

Frey et al., "Covalent attachment and derivatization of poly (L-lysine) monolayers on gold surfaces as characterized by polarization—modulation FT-IR spectroscopy," Analytical Chemistry, Sep. 15, 1996, 68(18):3187-93.

Hainfeld et al., "The use of gold nanoparticles to enhance radiotherapy in mice," Physics in Medicine & Biology, Sep. 3, 2004, 49(18):N309-15.

Haseltine et al., "Fatal complications after stereotactic body radiation therapy for central lung tumors abutting the proximal bronchial tree," Pract. Radiat. Oncol., Aug. 2016, 6(2):e27-e33.

Hepel et al., "Stereotactic Body Radiation Therapy Boost After Concurrent Chemoradiation for Locally Advanced Non-Small Cell Lung Cancer: A Phase 1 Dose Escalation Study," Int. J. Radiat. Oncol. Biol. Phys., Dec. 2016, 96(5):1021-1027, 27 pages.

Hepel et al., "Stereotactic body radiation therapy boost after concurrent chemoradiation for locally advanced non-small cell lung cancer: a phase 1 dose escalation study," International Journal of Radiation Oncology* Biology* Physics, Dec. 1, 2016, 96(5):1021, 26 Pages.

Herter-Sprie et al., "Image-guided radiotherapy platform using single nodule conditional lung cancer mouse models," Nature Communications, Dec. 18, 2014, 5:5870.

Hu et al., "Pm-149 DOTA bombesin analogs for potential radiotherapy: in vivo comparison with Sm-153 and Lu-177 labeled DO3A-amide-βAla-BBN (7-14) NH2," Nuclear Medicine and Biology, May 1, 2002, 29(4):423-30.

Jaffray et al., "Flat-panel cone-beam computed tomography for image-guided radiation therapy," International Journal of Radiation Oncology, Biology, Physics, Aug. 2002, 53:1337-1349.

Kao et al., "Long-residence-time nano-scale liposomal iohexol for X-ray-based blood pool imaging," Academic Radiology. May 1, 2003, 10(5):475-83.

Kong et al, "High-dose radiation improved local tumor control and overall survival in patients with inoperable/unresectable non-small-cell lung cancer: Long-term results of a radiation dose escalation study," International Journal of Radiation Onocology, Biology, Phyiscs, Oct. 2005, 63(2):324-333.

Kotb et al., "Safety evaluation and imaging properties of gadolinium-based nanoparticles in nonhuman primates," Scientific Reports, Oct. 11, 2016, 6:35053, 9 Pages.

Kunjachan et al., "Nanoparticle mediated tumor vascular disruption: a novel strategy in radiation therapy," Nano Letters, Oct. 6, 2015, 15(11):7488-96.

Laurent et al., "Minor changes in the macrocyclic ligands but major consequences on the efficiency of gold nanoparticles designed for radiosensitization," Nanoscale, 2016, 8(23):12054-65.

Le Duc et al., "Toward an image-guided microbeam radiation therapy using gadolinium-based nanoparticles," ACS Nano, Nov. 9, 2011, 5(12):9566-74.

Lee et al., "Nano-sized CT contrast agents," Advanced Materials, May 21, 2013, 25(19):2641-60.

Li et al., "Development of an in vitro model for assessing the in vivo stability of lanthanide chelates," Nuclear Medicine and Biology, Feb. 1, 2001, 28(2)445-54.

Manohar et al., "Quantitative imaging of gold nanoparticle distribution in a tumor-bearing mouse using benchtop x-ray fluorescence computed tomography," Scientific Reports, Feb. 25, 2016, 6:22079, 10 Pages.

McMahon et al., "Biological consequences of nanoscale energy deposition near irradiated heavy atom nanoparticles," Scientific reports, Jun. 20, 2011, 1:18, 9 pages.

McMahon et al., "Optimising element choice for nanoparticle radiosensitisers," Nanoscale, 2016;8(1):581-9.

Miller et al., "Cancer treatment and survivorship statistics, 2016," CA: A Cancer Journal for Clinicians, Jul. 2016, 66(4):271-89.

Movsas et al., "Quality of life analysis of a radiation dose-escalation study of patients with non-small-cell lung cancer: a secondary analysis of the radiation therapy oncology group 0617 randomized clinical trial," JAMA Oncology, Mar. 2016, 2(3):359-367.

Na et al., "Development of a T1 contrast agent for magnetic resonance imaging using MnO nanoparticles," Angewandte Chemie International Edition, Jul. 9, 2007, 46(28):5397-401.

Ning et al, "Dinitroazetidines Are a Novel Class of Anticancer Agents and Hypoxia-Activated Radiation Sensitizers Developed from Highly Energetic Materials," Cancer Res., May 2012, 72(10):2600-2608.

Noel et al., "Comparison of onboard low-field magnetic resonance imaging versus onboard computed tomography for anatomy visualization in radiotherapy," Acta. Oncol., Jul. 2015, 54(9):1474-1482.

Pan et al., "Gold nanoparticles of diameter 1.4 nm trigger necrosis by oxidative stress and mitochondrial damage," Small, Sep. 18, 2009, 5(18):2067-76.

PCT International Preliminary Report on Patentability for International Appln. PCT/US2017/065365, dated Jun. 20, 2019, 7 Pages.

(56) References Cited

OTHER PUBLICATIONS

PCT International Search Report and Written Opinion for International Appln. PCT/US2017/065365, dated Mar. 5, 2018, 35 pages.
Que et al., "Fluorescence characteristics from microemulsion technique derived erbium (III) oxide nanocrystals," Materials Research Bulletin, Mar. 1, 2001, 36(5-6):889-95.
Que et al., "Yellow-to-violet upconversion in neodymium oxide nanocrystal/titania/ormosil composite sol-gel thin films derived at low temperature," Journal of Applied Physics, Nov. 1, 2001, 90(9):4865-7.
Ramroth et al., "Dose and Fractionation in Radiation Therapy of Curative Intent for Non-Small Cell Lung Cancer: Meta-Analysis of Randomized Trials," Int. J. Radiat. Oncol. Biol. Phys., Nov. 2016, 96(4):736-747.
Retif et al., "Nanoparticles for radiation therapy enhancement: the key parameters," Theranostics, 2015, 5(9):1030-45.
Sancey et al., "Long-term in vivo clearance of gadolinium-based AGuIX nanoparticles and their biocompatibility after systemic injection," ACS Nano, Feb. 26, 2015, 9(3):2477-88.
Sancey et al., "The use of theranostic gadolinium-based nanoprobes to improve radiotherapy efficacy," The British Journal of Radiology, Aug. 7, 2014, 87(1041):20140134.
Siegel et al., "Cancer statistics, 2016," A Cancer Journal for Clinicians, 2016, 66(1):7-30.
Song et al., "Core-shell MnSe@ Bi2Se3 fabricated via a cation exchange method as novel nanotheranostics for multimodal imaging and synergistic thermoradiotherapy," Advanced Materials, Oct. 2015, 27(40):6110-7.
Stoia et al., "Silica matrices for embedding of magnetic nanoparticles," Journal of Sol-Gel Science and Technology, Apr. 1, 2012, 62(1):31-40.
Urtasun et al., "Phase 1 study of high-dose metronidazole: a specific in vivo and in vitro radiosensitizer of hypoxic cells," Radiology, Oct. 1975, 117(1):129-33.
Van Schooneveld et al., "A fluorescent, paramagnetic and PEGylated gold/silica nanoparticle for MRI, CT and fluorescence imaging," Contrast Media & Molecular Imaging, Jul. 2010, 231-6.
Zhu et al. "Nanoparticle-Based Systems for T1-Weighted Magnetic Resonance Imaging Contrast Agents" International Journal of Molecular Sciences. 2013, vol. 14, p. 10591-10607.
canver.gov. "Radiosensitizing Agent," pulled Oct. 1, 2021 from URL <https://www.cancer.gov/publications/dictionaries/cancer-terms/def/radiosensitizing-agent>, 1 page.
CN Office Action in Chinese Appln. No. 201780085765.1, dated Jul. 2, 2021, 22 pages (with English translation).

* cited by examiner

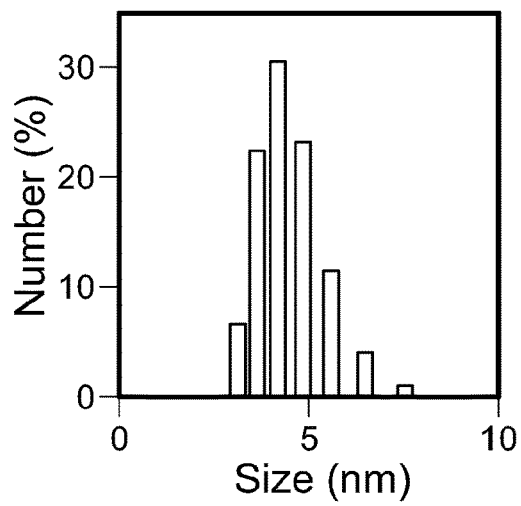
Figure 1C
| Massic Concentration (%) | | |
|---|---|---|
| Element | SiGdNP | SiBiGdNP |
| Si | 11.3 | 14 |
| C | 23.5 | 23.7 |
| N | 7.05 | 6.9 |
| Gd | 8.1 | 8.1 |
| Bi | N/A | 6.1 |
Figure 1D
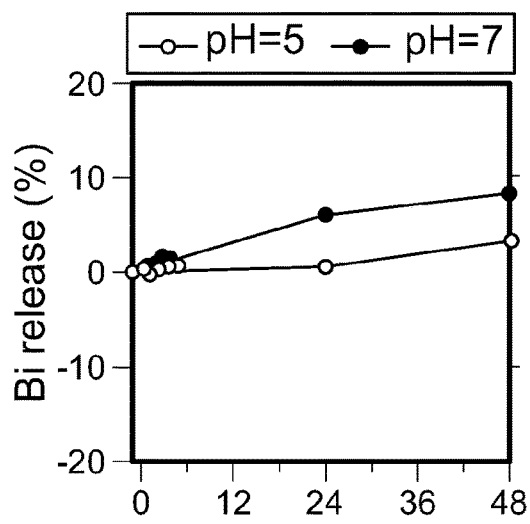
Figure 1E

BISMUTH-GADOLINIUM NANOPARTICLES

CROSS-REFERENCE TO RELATED APPLICATIONS

This application is a national stage application under 35 U.S.C. § 371 of International Application No. PCT/US2017/065365, filed on Dec. 8, 2017, which claims the benefit of U.S. Provisional Application Ser. No. 62/431,607, filed Dec. 8, 2016, the disclosure of which is incorporated herein by reference in its entirety.

FEDERALLY SPONSORED RESEARCH OR DEVELOPMENT

This invention was made with Government support under Grant No. R21 Ca188833, awarded by the National Institutes of Health. The Government has certain rights in the invention.

TECHNICAL FIELD

The present application provides nanoparticle compositions comprising one or more high atomic number ions that are useful for imaging a disease in a subject as well as radiosensitizing a disease in a subject (e.g., radiosensitizing a cancer in the subject).

BACKGROUND

Clinical radiation therapy is a non-invasive means of killing cancer cells and effectively reducing tumor burden. This method of treatment is prescribed for more than 50% of cancer patients. While radiation therapy is highly effective for the majority of cancer patients (see e.g., Miller et al, *A Cancer Journal for Clinicians*, 2016, 66:7) the nonspecificity of the irradiation can result in toxicity to surrounding tissues (see e.g., Barnett et al, *Nature Review*, 2009, 9:134). This is can be problematic for patients with tumors that require high radiation doses or with tumors that are difficult to target with image-guidance (see e.g., Movsas et al, *JAMA Oncology*, 2016, 2:359; and Kong et al, *International Journal of Radiation Onocology, Biology, Phyiscs*, 2005, 63:324).

SUMMARY

The present application provides, inter alia, a composition comprising:

a nanoparticle core comprising one or more first linking groups covalently bonded to a first ligand and one or more second linking groups covalently bonded to a second ligand;

wherein one or more of the first ligands are complexed to $Gd^{3+}$ ions and one or more of the second ligands are complexed to $Bi^{3+}$ ions.

In some embodiments, the nanoparticle core is a silica core. In some embodiments, the nanoparticle core is a polysiloxane core.

In some embodiments, the one or more first linking groups each comprise a $C_{1-10}$ alkylamine covalently bonded to the first ligand. In some embodiments, each of the first ligands is independently selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC). In some embodiments, each of the first ligands is independently selected from the group consisting of:

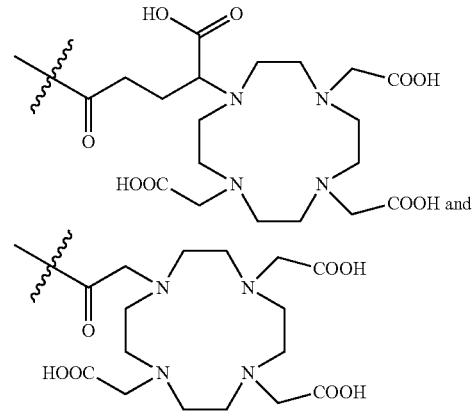

wherein ∿∿∿ indicates the bond connecting the first ligand to the first linking group. In some embodiments, each of the first ligands is

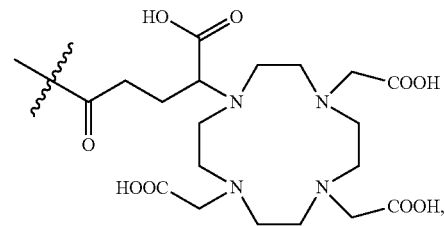 [SMILES: *C(=O)CCC(C(=O)O)N1CCN(CC(=O)O)CCN(CC(=O)O)CCN(CC(=O)O)CC1]

wherein ∿∿∿ indicates the bond connecting the first ligand to the first linking group.

In some embodiments, the one or more second linking groups each comprise a $C_{1-10}$ alkylamine covalently bonded to the second ligand. In some embodiments, each of the second ligands is independently selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC). In some embodiments, each of the second ligands is independently selected from the group consisting of:

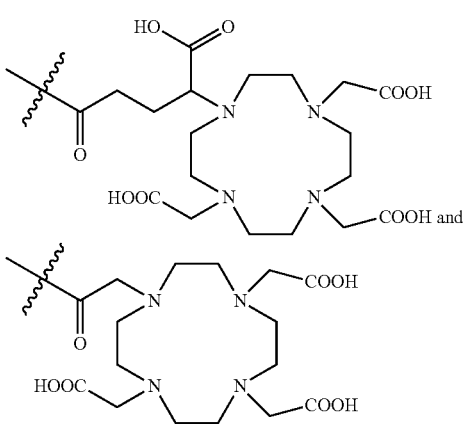

wherein ⌇⌇⌇ indicates the bond connecting the second ligand to the second linking group. In some embodiments, each of the second ligands is

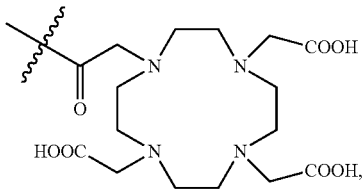 [SMILES: *C(=O)CN1CCN(CC(=O)O)CCN(CC(=O)O)CCN(CC(=O)O)CC1]

wherein ⌇⌇⌇ indicates the bond connecting the second ligand to the second linking group.

In some embodiments, greater than about 20% of the first ligands are complexed to the $Gd^{3+}$ ions. In some embodiments, greater than about 20% of the second ligands are complexed to the $Bi^{3+}$ ions. In some embodiments, the composition comprises a ratio of $Gd^{3+}$ ions:$Bi^{3+}$ ions of from about 1:1 to about 2:1. In some embodiments, the nanoparticle comprises from about 5 to about 15 $Gd^{3+}$ ions and from about 1 to about 10 $Bi^{3+}$ ions.

In some embodiments, the hydrodynamic diameter of the nanoparticle is from about 2 nm to about 8 nm. In some embodiments, the hydrodynamic diameter of the composition is from about 3 nm to about 6 nm.

In some embodiments, the composition is suitable for intravenous or nasal administration.

The present application further provides a method of treating a cancer in a subject, the method comprising:
i) administering to the subject a therapeutically effective amount of a composition provided herein; and
ii) administering one or more doses of radiation to the subject.

The present application further provides a method of imaging a cancer in a subject, the method comprising:
i) administering to the subject a therapeutically effective amount of a composition provided herein; and
ii) imaging the subject with a suitable imaging technique.

The present application further provides a method of treating a cancer in a subject, the method comprising:
i) administering to the subject a therapeutically effective amount of a composition provided herein;
ii) imaging the subject with a suitable imaging technique; and
iii) administering one or more doses of radiation to the subject.

The present application further provides a method of monitoring treatment of a cancer in a subject, the method comprising:
i) administering to the subject a therapeutically effective amount of a composition provided herein;
ii) imaging the subject with a suitable imaging technique; and
iii) administering one or more doses of radiation to the subject.

In some embodiments, the methods provided herein further comprise administering an additional therapeutically effective amount of the composition to the subject after step ii) and prior to step iii).

In some embodiments, the methods provided herein further comprise imaging the subject with a suitable imaging technique after step iii).

In some embodiments, the composition provided herein radiosensitizes the cancer.

In some embodiments, the cancer is a solid tumor. In some embodiments, the cancer is selected from the group consisting of lung cancer, brain cancer, cancer of the head and neck, cervical cancer, pancreatic cancer, breast cancer, prostate cancer, liver cancer, colon cancer, endometrial cancer, bladder cancer, skin cancer, renal cancer, and gastric cancer.

In some embodiments, the imaging is performed using magnetic resonance imaging, computed tomography imaging, positron emission tomography imaging, or any combination thereof.

The present application further provides a process of preparing a composition of provided herein, the process comprising reacting composition A with a $Bi^{3+}$ salt in the presence of an acid to form the composition, wherein composition A comprises:
a nanoparticle core comprising one or more first linking groups covalently bonded to a first ligand and one or more second linking groups covalently bonded to a second ligand;
wherein one or more of the first ligands are complexed to $Gd^{3+}$ ions.

In some embodiments, the acid is hydrochloric acid.

In some embodiments, the $Bi^{3+}$ salt is $BiCl_3$.

In some embodiments, the reacting of composition A with a $Bi^{3+}$ salt is performed in the presence of a solvent. In some embodiments, the solvent is water.

In some embodiments, the reacting of composition A with a $Bi^{3+}$ salt is performed a temperature of from about 40° C. to about 80° C.

In some embodiments, composition A is prepared according to a process comprising reacting composition B with a second reactive ligand to form composition A, wherein composition B comprises:
a nanoparticle core comprising one or more first linking groups covalently bonded to a first ligand and one or more second linking groups;
wherein one or more of the first ligands are complexed to $Gd^{3+}$ ions.

In some embodiments, the reacting of composition B with the second reactive ligand is performed in the presence of a solvent. In some embodiments, the solvent is a mixture of dimethyl sulfoxide and water. In some embodiments, the reacting of composition B with the second reactive ligand is performed a pH of from about 7 to about 8.

In some embodiments, composition B is prepared according to a process comprising contacting composition C with water to form composition B, wherein composition C comprises a bi-layer nanoparticle core comprising one or more first linking groups covalently bonded to a first ligand.

In some embodiments, the bi-layer nanoparticle core comprises a $Gd_2O_3$ layer.

In some embodiments, the reaction of composition C with the water dissolves the bi-layer nanoparticle core, thereby forming the nanoparticle core and the one or more first linking groups covalently bonded to a first ligand, wherein one or more of the first ligands are complexed to $Gd^{3+}$ ions.

In some embodiments, composition C is prepared according to a process comprising reacting a first reactive ligand with the bi-layer nanoparticle core comprising one or more first linking groups to form composition C.

In some embodiments, the bi-layer nanoparticle core comprises $Gd_2O_3$ and one or more $C_{1-10}$ alkylamine groups. In some embodiments, the bi-layer nanoparticle core comprises a $Gd_2O_3$ layer and a silica layer. In some embodiments, the bi-layer nanoparticle core comprises a $Gd_2O_3$ layer and a polysiloxane layer.

In some embodiments, the first reactive ligand is selected from the group consisting of:

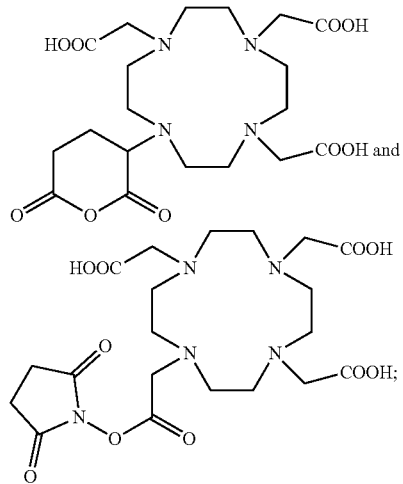

or a mixture thereof.

In some embodiments, the first reactive ligand is

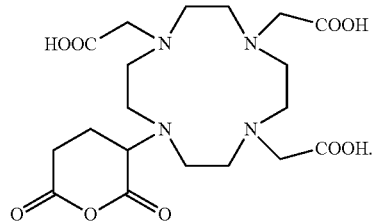 [SMILES: O=C(O)CN1CCN(CC(=O)O)CCN(C2CCC(=O)OC2=O)CCN(CC(=O)O)CC1]

In some embodiments, each of the first ligands is

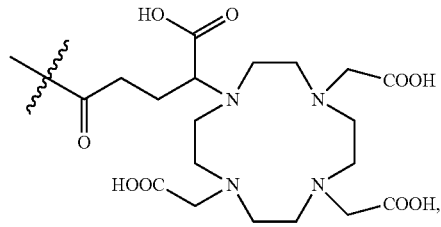 [SMILES: *C(=O)CCC(C(=O)O)N1CCN(CC(=O)O)CCN(CC(=O)O)CCN(CC(=O)O)CC1]

wherein ∿∿∿ indicates the bond connecting the first ligand to the first linking group.

In some embodiments, the second reactive ligand is selected from the group consisting of:

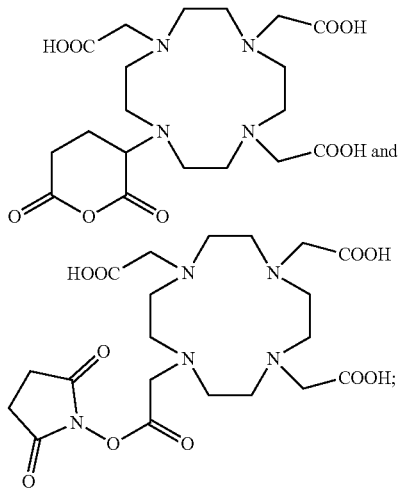

or a mixture thereof.

In some embodiments, the second reactive ligand is

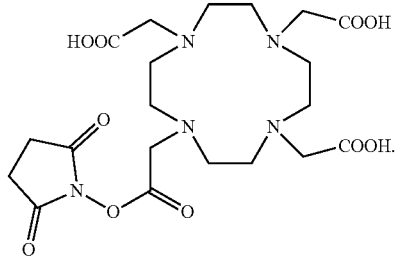 [SMILES: O=C(O)CN1CCN(CC(=O)O)CCN(CC(=O)ON2C(=O)CCC2=O)CCN(CC(=O)O)CC1]

In some embodiments, each of the second ligands is

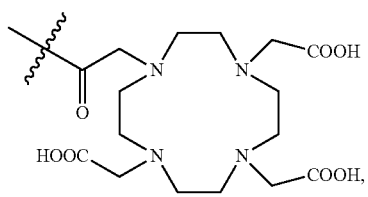 [SMILES: *C(=O)CN1CCN(CC(=O)O)CCN(CC(=O)O)CCN(CC(=O)O)CC1]

wherein ∿∿∿ indicates the bond connecting the second ligand to the second linking group.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 1C shows dynamic light scattering measurements of a SiBiGdNP particle of size 4.5+/−0.9 nm.

FIG. 1D shows the results of elemental characterization by ICP-OES of a nanoparticle composition before and after the grafting of $Bi^{3+}$.

FIG. 1E shows percent release of free $Bi^{3+}$ atoms measured by absorbance (305 nm) at pH=5 and pH=7 over 48 h.

DETAILED DESCRIPTION

Figure 1A:
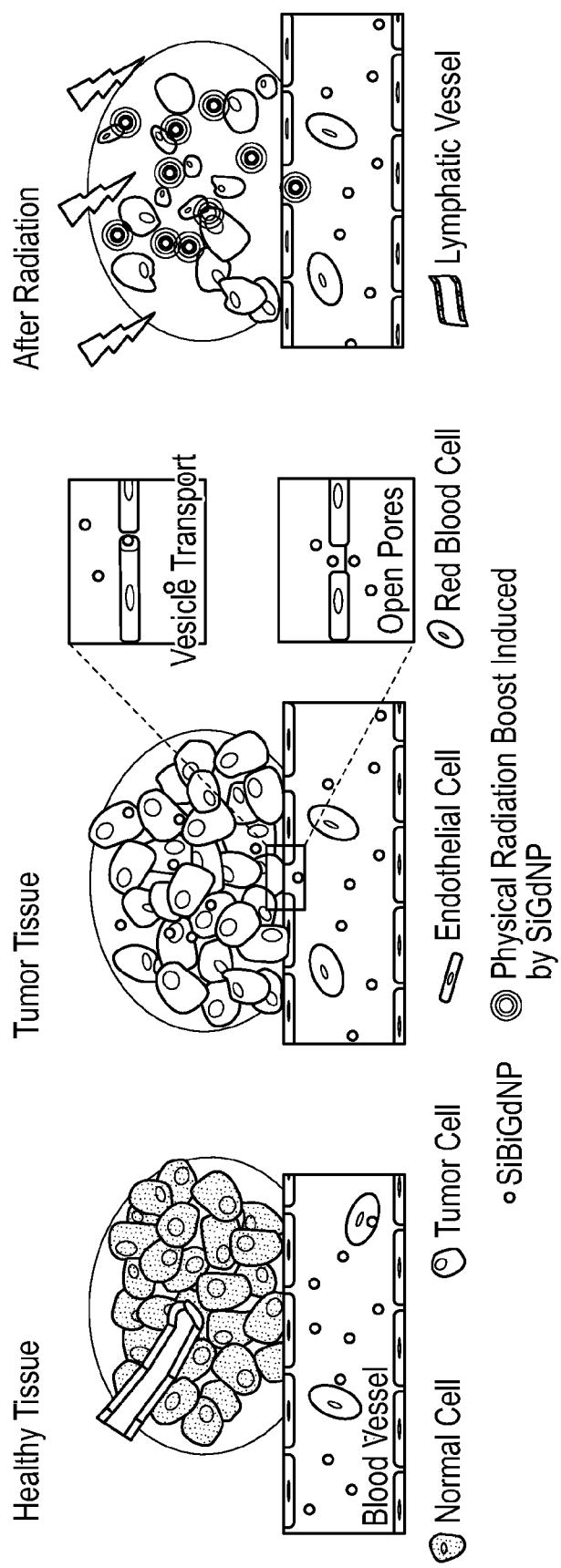
FIG. 1A shows a schematic representation of uptake of a silica-based bismuth-gadolinium nanoparticle in a tumor by enhanced-permeability and retention (EPR) effect and the efficacy of the nanoparticle after external radiation.

It has been demonstrated that dose escalation in non-small cell lung cancer (NSCLC) cases improves the overall survival of patients but at the risk of toxicity in the lungs and heart (see e.g., Hepel et al, *Int. J. Radiat. Oncol. Biol. Phys.* 2016, 96(5):1021-1027; Ramroth et al, *Int. J. Radiat. Oncol. Biol. Phys.* 2016, 96:736; Brower et al, *Ann. Oncol.* 2016, 27:1887). For centrally located early stage NSCLC tumors, proximity of the mediastinum can preclude the use of ablative radiation techniques like stereotactic body radiation therapy (SBRT) (see e.g., Haseltine et al, *Pract. Radiat. Oncol.* 2016, 6:e27). This is exacerbated by the large movements of the tumor due to respiration during therapy (see e.g., De Ruysscher et al, *Lancet Oncol.* 2016, 17(12):1625-1626; Bissonnette et al, *Int. J Radiat. Oncol. Biol. Phys.* 2009, 73:927). Non-invasive imaging modalities can be used to improve the precision and the accuracy of clinical radiation treatment (see e.g., Dawson et al, *Oncologist*, 2010, 15:338). To mitigate off-target toxicity, image-guided radiation therapy (IGRT) has been developed to localize tumors with cone-beam computed tomography (CBCT) images acquired just prior to therapeutic irradiation (see e.g., Jaffray et al, *International Journal of Radiation Oncology, Biology, Physics*, 2002, 53:1337). More recently, the use of magnetic resonance (MR) image-guided radiation therapy has enabled more precise and accurate localization and treatment, especially for tumors embedded within soft tissues (see e.g., Dawson et al, *Journal of Clinical Oncology: Official Journal of the American Society of Clinical Oncology*, 2007, 25:938; and Noel et al, *Acta. Oncol.* 2015, 54:1474). While these methods increase dose conformality to the target, some irradiation of healthy tissues is unavoidable.

Radiosensitizers have been developed to amplify the effects of radiation within tumor cells. Non-targeted chemical radiosensitizers have resulted in some severe toxicities (see e.g., Urtasun et al, *Cancer Res.* 2012, 72:2600). To solve this problem, high atomic number nanoparticles have been designed as next-generation radiosensitizers or radiation dose amplification agents. These nanoparticles are inert and only activated on-demand by the therapeutic radiation beam (see e.g., McMahon et al, *Nanoscale*, 2016, 8:581). For example, both gadolinium (Z=64) and bismuth (Z=83) produce photoelectrons and Auger electrons after interaction with a clinical 6 MV radiation beam (see e.g., McMahon et al, *Nanoscale*, 2016, 8:581). In this approach, high atomic number atoms in the nanoparticles interact with the incident photons from the radiation beam and generate secondary photoelectrons or Auger electrons which deposit a boost of energy locally (within a few microns of the nanoparticle) (see e.g., Retif et al, *Theranostics*, 2015, 5:1030; and McMahon et al, *Scientific Reports*, 2011, 1:18). Induced biological stress in nearby cells may also increase the local efficacy of the therapy (see e.g., Pan et al, *Small*, 2009, 5:2067). Coupling this novel therapy with quantitative volumetric image guidance will enable further optimization and individualization of radiation delivery to maximize therapeutic effect.

Gold nanoparticles are often proposed for medical purposes due to the ease of surface modification and relative non-toxicity (see e.g., Daniel et al, *Chem. Rev.* 2004, 104:293; Hainfeld et al, *Phys. Med. Biol.* 2004, 49:N309; Laurent et al, *Nanoscale*, 2016, 8:12054; and Kunjachan et al, *Nano. Lett.* 2015, 15:7488). At the concentrations used for IV injection, in vivo x-ray contrast with gold nanoparticles is not feasible, necessitating the use of other imaging modalities. Optical agents have been used for pre-clinical studies, but this modality is very limited clinically (see e.g., Kunjachan et al, *Nano. Lett.* 2015, 15:7488; and Manohar et al, *Sci. Rep.* 2016, 6:22079). To address this challenge, gadolinium-based nanoparticles have been designed and tested (see e.g., Detappe et al, *J. Control Release*, 2016, 238:103; Sancey et al, *ACS Nano*, 2015, 9:2477; and Le Duc et al, *ACS Nano*, 2011, 5:9566). The gadolinium atoms can provide both MRI contrast and radiation dose amplification. However, the probability for photons to undergo a photoelectric interaction with a given atom is proportionate to $Z^3$, where Z is the atomic number of the atom. Therefore, gadolinium ($Z_{Gd}$=64) has a lower probability of interaction than gold ($Z_{Au}$=79) or bismuth ($Z_{Bi}$=83), for example. Bismuth-based nanoparticles have been mainly designed to act as CT contrast agents (see e.g., Lee et al, *J. Biomed. Mater. Res. B Appl. Biomater.* 2013, 101:131). Recently, their efficacy as radiosensitizers was evaluated in vitro with promising results (see e.g., Alqathami et al, *J. Biomed. Nanotechnol.* 2016, 12:464).

Accordingly, the present application provides a new class of theranostic nanoparticles that enable MR and CT contrast while simultaneously amplifying radiation dose under clinical irradiation conditions (see e.g., FIG. 1A). The compositions provided herein comprise, for example, $Gd^{3+}$ and $Bi^{3+}$ ions that are sequestered by pendant ligands (e.g., DOTA ligands). The gadolinium ions allow the nanoparticle composition to act as a positive MRI $T_1$ contrast agent while the bismuth ions provide CT contrast. In addition, both the gadolinium and bismuth ions have high atomic numbers ($Z_{Gd}$=64 and $Z_{Bi}$=83), thereby facilitating radiation dose amplification. The structure of the compositions allows for visibility in a low concentration range for both MRI and CT imaging techniques, thereby increasing clinical utility.

Nanoparticle Compositions

The present application provides a composition, comprising:

a nanoparticle core comprising one or more first linking groups covalently bonded to a first ligand and one or more second linking groups covalently bonded to a second ligand;

wherein one or more of the first ligands are complexed to a first ion and one or more of the second ligands are complexed to a second ion, wherein the first and second ions each have an atomic number greater than 50.

In some embodiments the first and second ions have a difference in atomic number of at least 10. In some embodiments the first and second ions have a difference in atomic number of from 10 to 30, for example, 10 to 25, 10 to 20, 10 to 15, 15 to 30, 15 to 25, 15 to 20, 20 to 30, 20 to 25, or 25 to 30. In some embodiments, the first ion is $Gd^{3+}$. In some embodiments, the second ion is $Bi^{3+}$.

The present application further provides a composition, comprising:

a nanoparticle core comprising one or more first linking groups covalently bonded to a first ligand and one or more second linking groups covalently bonded to a second ligand;

wherein one or more of the first ligands are complexed to $Gd^{3+}$ ions and one or more of the second ligands are complexed to $Bi^{3+}$ ions.

In some embodiments, the nanoparticle core is a silica core. In some embodiments, the nanoparticle core is a polysiloxane core.

In some embodiments, the one or more first linking groups each comprise a $C_{1-10}$ alkylamine covalently bonded to the first ligand. In some embodiments, the one or more first linking groups each comprise a $C_{1-10}$ alkylamine covalently bonded to the first ligand, wherein the first ligand is covalently bonded to the nitrogen atom of the $C_{1-10}$ alkylamine.

In some embodiments, each of the first ligands is independently selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1, 2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyldiamine triacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC).

In some embodiments, each of the first ligands is independently selected from the group consisting of:

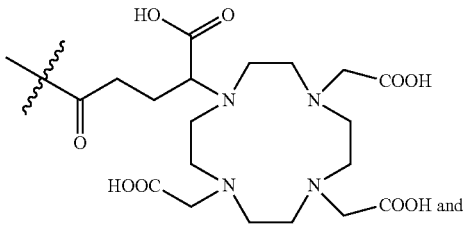

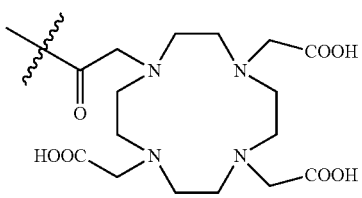

wherein ⌇⌇⌇ indicates the bond connecting the first ligand to the first linking group.

In some embodiments, each of the first ligands is

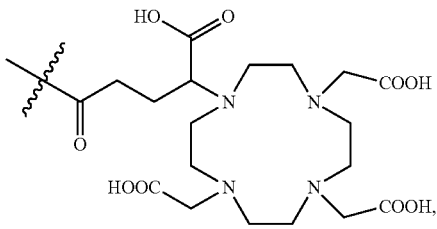 [SMILES: *C(=O)CCC(C(=O)O)N1CCN(CC(=O)O)CCN(CC(=O)O)CCN(CC(=O)O)CC1]

wherein ⌇⌇⌇ indicates the bond connecting the first ligand to the first linking group.

In some embodiments, the one or more second linking groups each comprise a $C_{1-10}$ alkylamine covalently bonded to the second ligand. In some embodiments, the one or more second linking groups each comprise a $C_{1-10}$ alkylamine covalently bonded to the second ligand, wherein the second ligand is covalently bonded to the nitrogen atom of the $C_{1-10}$ alkylamine.

In some embodiments, each of the second ligands is independently selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC).

In some embodiments, each of the second ligands is independently selected from the group consisting of:

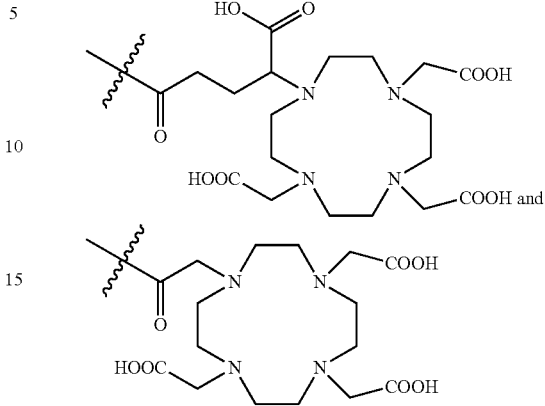

wherein ⌇⌇⌇ indicates the bond connecting the second ligand to the second linking group.

In some embodiments, each of the second ligands is

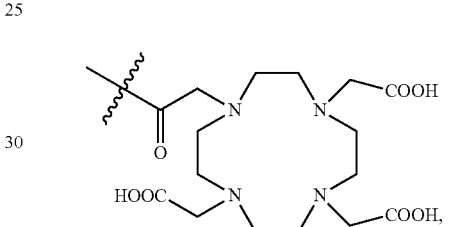

wherein ⌇⌇⌇ indicates the bond connecting the second ligand to the second linking group.

In some embodiments, each of the first linking groups are the same. In some embodiments, each of the first ligands are the same.

In some embodiments, each of the second linking groups are the same. In some embodiments, each of the second ligands are the same.

In some embodiments, each of the first linking groups and each of the second linking groups are the same group. In some embodiments, each of the first linking groups are the same group, each of the second linking groups are the same group, and the first linking group and the second linking group are not the same group.

In some embodiments, each of the first ligands and each of the second ligands are the same group. In some embodiments, each of the first ligands are the same group, each of the second ligands are the same group, and the first ligand and second ligand are not the same group.

In some embodiments, greater than about 10% of the first ligands are complexed to the first ions, for example, greater than about 15%, greater than about 25%, greater than about 50%, greater than about 75%, greater than about 90%, greater than about 95%, or greater than about 99%. In some embodiments, greater than about 20% of the first ligands are complexed to the first ions. In some embodiments, greater than about 10% of the first ligands are complexed to the $Gd^{3+}$ ions, for example, greater than about 15%, greater than about 25%, greater than about 50%, greater than about 75%, greater than about 90%, greater than about 95%, or greater than about 99%. In some embodiments, greater than about 20% of the first ligands are complexed to the $Gd^{3+}$ ions.

In some embodiments, about 10% to about 99% of the first ligands are complexed to the first ions, for example, about 10% to about 95%, about 10% to about 75%, about 10% to about 50%, about 10% to about 25%, about 10% to about 15%, about 15% to about 99%, about 15% to about 95%, about 15% to about 75%, about 15% to about 50%, about 15% to about 25%, about 25% to about 99%, about 25% to about 95%, about 25% to about 75%, about 25% to about 50%, about 50% to about 99%, about 50% to about 95%, about 50% to about 75%, about 75% to about 99%, about 75% to about 95%, or about 95% to about 99%. In some embodiments, about 10% to about 99% of the first ligands are complexed to the $Gd^{3+}$ ions, for example, about 10% to about 95%, about 10% to about 75%, about 10% to about 50%, about 10% to about 25%, about 10% to about 15%, about 15% to about 99%, about 15% to about 95%, about 15% to about 75%, about 15% to about 50%, about 15% to about 25%, about 25% to about 99%, about 25% to about 95%, about 25% to about 75%, about 25% to about 50%, about 50% to about 99%, about 50% to about 95%, about 50% to about 75%, about 75% to about 99%, about 75% to about 95%, or about 95% to about 99%.

In some embodiments, greater than about 10% of the second ligands are complexed to the second ions, for example, greater than about 15%, greater than about 25%, greater than about 50%, greater than about 75%, greater than about 90%, greater than about 95%, or greater than about 99%. In some embodiments, greater than about 20% of the second ligands are complexed to the second ions. In some embodiments, greater than about 10% of the second ligands are complexed to the $Bi^{3+}$ ions, for example, greater than about 15%, greater than about 25%, greater than about 50%, greater than about 75%, greater than about 90%, greater than about 95%, or greater than about 99%. In some embodiments, greater than about 20% of the second ligands are complexed to the $Bi^{3+}$ ions.

In some embodiments, greater than about 20% of the first ligands are complexed to the first ions and greater than about 20% of the second ligands are complexed to the second ions. In some embodiments, greater than about 20% of the first ligands are complexed to the $Gd^{3+}$ ions and greater than about 20% of the second ligands are complexed to the $Bi^{3+}$ ions.

In some embodiments, about 10% to about 99% of the first ligands are complexed to the first ions, for example, about 10% to about 95%, about 10% to about 75%, about 10% to about 50%, about 10% to about 25%, about 10% to about 15%, about 15% to about 99%, about 15% to about 95%, about 15% to about 75%, about 15% to about 50%, about 15% to about 25%, about 25% to about 99%, about 25% to about 95%, about 25% to about 75%, about 25% to about 50%, about 50% to about 99%, about 50% to about 95%, about 50% to about 75%, about 75% to about 99%, about 75% to about 95%, or about 95% to about 99%.

In some embodiments, about 10% to about 99% of the first ligands are complexed to the $Gd^{3+}$ ions, for example, about 10% to about 95%, about 10% to about 75%, about 10% to about 50%, about 10% to about 25%, about 10% to about 15%, about 15% to about 99%, about 15% to about 95%, about 15% to about 75%, about 15% to about 50%, about 15% to about 25%, about 25% to about 99%, about 25% to about 95%, about 25% to about 75%, about 25% to about 50%, about 50% to about 99%, about 50% to about 95%, about 50% to about 75%, about 75% to about 99%, about 75% to about 95%, or about 95% to about 99%.

In some embodiments, the composition comprises a ratio of first ions:second ions of from about 1:1 to about 10:1, for example 1:1, 2:1, 3:1, 4:1, 5:1, 6:1, 7:1, 8:1, 9:1, or 10:1. In some embodiments, the composition comprises a ratio of first ions:second ions of from about 1:1 to about 2:1, for example, 1:1, 1:2, 1:3, 1:4, 1:5, 1:6, 1:7, 1:8, 1:9, or 1:10. In some embodiments, the composition comprises a ratio of first ions:second ions of from about 1:1 to about 1:2.

In some embodiments, the composition comprises a ratio of $Gd^{3+}$ ions:$Bi^{3+}$ ions of from about 1:1 to about 10:1, for example 1:1, 2:1, 3:1, 4:1, 5:1, 6:1, 7:1, 8:1, 9:1, or 10:1. In some embodiments, the composition comprises a ratio of $Gd^{3+}$ ions:$Bi^{3+}$ ions of from about 1:1 to about 2:1, for example, 1:1, 1:2, 1:3, 1:4, 1:5, 1:6, 1:7, 1:8, 1:9, or 1:10. In some embodiments, the composition comprises a ratio of $Gd^{3+}$ ions:$Bi^{3+}$ ions of from about 1:1 to about 1:2. In some embodiments, the composition comprises a ratio of $Gd^{3+}$ ions:$Bi^{3+}$ ions of from about 1:1 to about 2:1.

In some embodiments, the nanoparticle comprises from about 1 to about of the first ions, for example, about 1 to about 15, about 1 to about 10, about 1 to about 5, about 5 to about 20, about 5 to about 15, about 5 to about 10, about 10 to about 20, about 10 to about 15, or about 10 to about 20 of the first ions. In some embodiments, the nanoparticle comprises from about 5 to about 15 of the first ions.

In some embodiments, the nanoparticle comprises from about 1 to about of the second ions, for example, about 1 to about 15, about 1 to about 10, about 1 to about 5, about 5 to about 20, about 5 to about 15, about 5 to about 10, about 10 to about 20, about 10 to about 15, or about 10 to about 20 of the second ions. In some embodiments, the nanoparticle comprises from about 5 to about 15 of the second ions.

In some embodiments, the nanoparticle comprises from about 5 to about 15 of the first ions and from about 1 to about 10 of the second ions.

In some embodiments, the nanoparticle comprises from about 1 to about 20 $Gd^{3+}$ ions, for example, about 1 to about 15, about 1 to about 10, about 1 to about 5, about 5 to about 20, about 5 to about 15, about 5 to about 10, about 10 to about 20, about 10 to about 15, or about 10 to about 20 $Gd^{3+}$ ions. In some embodiments, the nanoparticle comprises from about 5 to about 15 $Gd^{3+}$ ions.

In some embodiments, the nanoparticle comprises from about 1 to about 20 $Bi^{3+}$ ions, for example, about 1 to about 15, about 1 to about 10, about 1 to about 5, about 5 to about 20, about 5 to about 15, about 5 to about 10, about 10 to about 20, about 10 to about 15, or about 10 to about 20 $Bi^{3+}$ ions. In some embodiments, the nanoparticle comprises from about 1 to about 10 $Bi^{3+}$ ions.

In some embodiments, the nanoparticle comprises from about 5 to about 15 $Gd^{3+}$ ions and from about 1 to about 10 $Bi^{3+}$ ions.

In some embodiments, the hydrodynamic diameter of the nanoparticle is from about 1 nm to about 10 nm, for example, about 1 nm to about 8 nm, about 1 nm to about 6 nm, about 1 nm to about 4 nm, about 1 nm to about 2 nm, about 2 nm to about 10 nm, about 2 nm to about 8 nm, about 2 nm to about 6 nm, about 2 nm to about 4 nm, about 4 nm to about 10 nm, about 4 nm to about 8 nm, about 4 nm to about 6 nm, about 6 nm to about 10 nm, about 6 nm to about 8 nm, or about 6 nm to about 8 nm. In some embodiments, the hydrodynamic diameter of the nanoparticle is from about 2 nm to about 8 nm. In some embodiments, the hydrodynamic diameter of the composition is from about 3 nm to about 6 nm.

In some embodiments, the composition is suitable for pulmonary administration (e.g., by inhalation or insufflation of powders or aerosols, including by nebulizer, intratracheal administration, or intranasal administration), oral administration, or parenteral administration (e.g., intravenous, intraarterial, subcutaneous, intraperitoneal, intramuscular or injection or infusion, intracranial, intrathecal, intraventricular administration, and the like). In some embodiments, the composition is suitable for intravenous or nasal administration.

Synthesis

The present application further provides processes for preparing the compositions provided herein. In some embodiments, the present application further provides a process of preparing a composition provided herein, the process comprising reacting composition A with a $Bi^{3+}$ salt in the presence of an acid to form the composition, wherein composition A comprises:

a nanoparticle core comprising one or more first linking groups covalently bonded to a first ligand and one or more second linking groups covalently bonded to a second ligand;

wherein one or more of the first ligands are complexed to $Gd^{3+}$ ions; and wherein the nanoparticle core, one or more first linking groups, first ligand, one or more second linking groups, and second ligand are as defined above for the compositions provided herein.

In some embodiments, the acid is a mineral acid. In some embodiments, the acid is hydrochloric acid. In some embodiments, the acid is aqueous hydrochloric acid.

In some embodiments, the $Bi^{3+}$ salt is selected from the group consisting of a halide salt (e.g., $BiCl_3$, $BiI_3$), a nitrate salt (e.g., $Bi(NO_3)_3$), an acetate salt (e.g., $Bi(OAc)_3$), and a trifluoromethanesulfonic acid salt (e.g., $Bi(OTf)_3$). In some embodiments, the $Bi^{3+}$ salt is a halide salt. In some embodiments, the $Bi^{3+}$ salt is $BiCl_3$ In some embodiments, the reacting of composition A with the $Bi^{3+}$ salt is performed in the presence of a solvent. In some embodiments, the solvent is selected from the group consisting of water, an alcohol (e.g., methanol, ethanol, n-propanol, iso-propanol, n-butanol, tert-butanol, and the like), and mixtures thereof. In some embodiments, the solvent is water. In some embodiments, the solvent is an alcohol. In some embodiments, the solvent is a mixture of water and alcohol.

In some embodiments, the reacting of composition A with the $Bi^{3+}$ salt is performed a temperature of from about 40° C. to about 80° C., for example, about 40° C. to about 70° C., about 40° C. to about 60° C., about 40° C. to about 50° C., about 50° C. to about 80° C., about 50° C. to about 70° C., about 50° C. to about 60° C., about 60° C. to about 80° C., about 60° C. to about 70° C., or from about 70° C. to about 80° C. In some embodiments, the reacting of composition A with the $Bi^{3+}$ salt is performed a temperature of from about 40° C. to about 60° C.

In some embodiments, composition A is prepared according to a process comprising reacting composition B with a second reactive ligand to form composition A, wherein composition B comprises:

a nanoparticle core comprising one or more first linking groups covalently bonded to a first ligand and one or more second linking groups;

wherein one or more of the first ligands are complexed to $Gd^{3+}$ ions.

In some embodiments, the reacting of composition B with the second reactive ligand is performed in the presence of a solvent. In some embodiments, the solvent is selected from the group consisting of water, an alcohol (e.g., methanol, ethanol, n-propanol, iso-propanol, n-butanol, tert-butanol, and the like), dimethyl sulfoxide, and mixtures thereof. In some embodiments, the solvent is water. In some embodiments, the solvent is an alcohol. In some embodiments, the solvent is an dimethyl sulfoxide. In some embodiments, the solvent is a mixture of water and alcohol. In some embodiments, the solvent is a mixture of alcohol and dimethyl sulfoxide. In some embodiments, the solvent is a mixture of dimethyl sulfoxide and water. In some embodiments, the solvent is a mixture of water, dimethyl sulfoxide, and an alcohol.

In some embodiments, the reacting of composition B with the second reactive ligand is performed a pH of from about 7 to about 8.

In some embodiments, composition B is prepared according to a process comprising contacting composition C with water to form composition B, wherein composition C comprises a bi-layer nanoparticle core comprising one or more first linking groups covalently bonded to a first ligand.

In some embodiments, the reaction of composition C with the water dissolves the bi-layer nanoparticle core, thereby forming the nanoparticle core and the one or more first linking groups covalently bonded to a first ligand, wherein one or more of the first ligands are complexed to $Gd^{3+}$ ions.

In some embodiments, composition C is prepared according to a process comprising reacting a first reactive ligand with the bi-layer nanoparticle core comprising one or more first linking groups to form composition C.

In some embodiments, the bi-layer nanoparticle core comprises a $Gd_2O_3$ layer. In some embodiments, the bi-layer nanoparticle core comprises $Gd_2O_3$ and one or more $C_{1-10}$ alkylamine groups. In some embodiments, the bi-layer nanoparticle core comprises a $Gd_2O_3$ layer and a silica layer. In some embodiments, the bi-layer nanoparticle core comprises a $Gd_2O_3$ layer and a polysiloxane layer.

In some embodiments, the first reactive ligand is selected from the group consisting of:

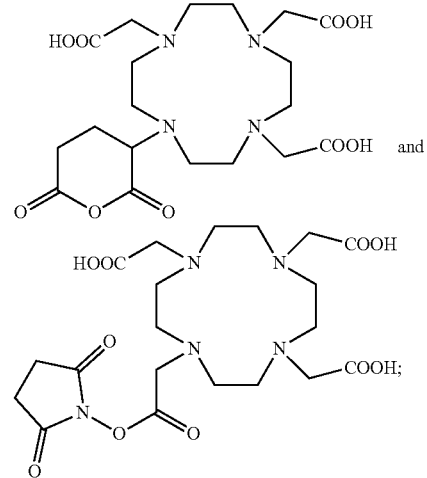

or a mixture thereof.

In some embodiments, the first reactive ligand is

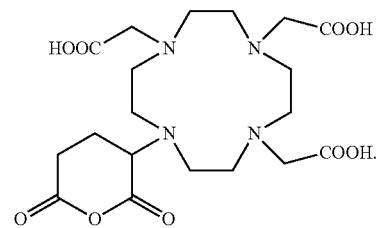 [SMILES: O=C(O)CN1CCN(CC(=O)O)CCN(C2CCC(=O)OC2=O)CCN(CC(=O)O)CC1]

In some embodiments, the second reactive ligand is selected from the group consisting of:

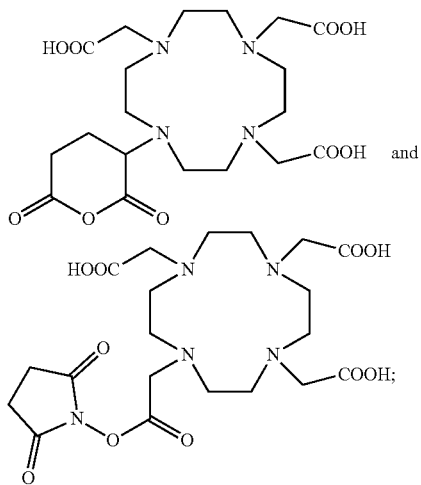

or a mixture thereof.

In some embodiments, the second reactive ligand is

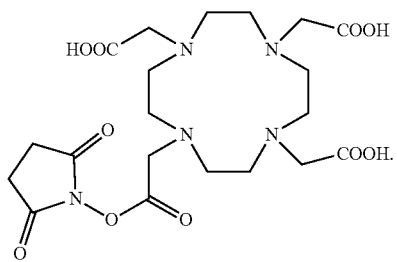 [SMILES: O=C(O)CN1CCN(CC(=O)O)CCN(CC(=O)ON2C(=O)CCC2=O)CCN(CC(=O)O)CC1]

In some embodiments, the first reactive ligand and the second reactive ligand are the same. In some embodiments, the first reactive ligand and the second reactive ligand are different.

Figure 1B:
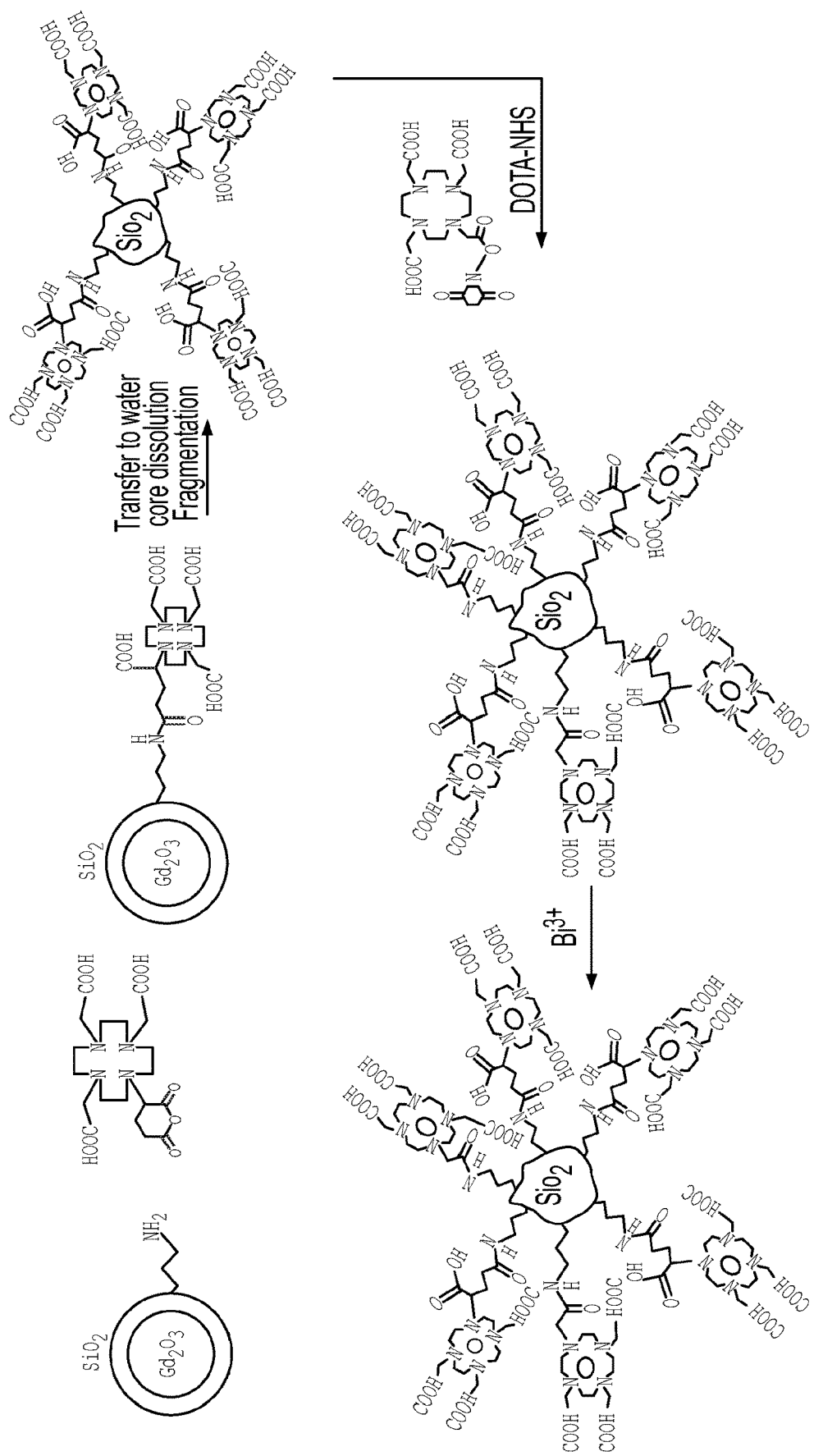
FIG. 1B shows a representative scheme of a $Gd_2O_3$ core and polysiloxane network grafted to DOTAGA ligands before transfer to water. A final fragmentation into sub-5 nm silica-based gadolinium nanoparticles (SiGdNP) was then performed. Afterwards, a DOTA-NHS structure was grafted at the surface of the SiGdNP particles to entrap the free $Bi^{3+}$ atoms into the final complex (figure not to scale).

In some embodiments, the compositions described herein are prepared according to the procedure shown in FIG. 1B.

Preparation of compositions described herein can further include, for example, the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkylamine" refers to a saturated hydrocarbon group substituted by an amino group, wherein the alkyl group has n to m carbon atoms. As used herein, the term "substituted" means that a hydrogen atom is removed and replaced by a substituent. It is to be understood that substitution at a given atom is limited by valency. In some embodiments, the alkyl group has 1 to 10, 1 to 6, or 1 to 4 carbon atoms. Exemplary alkylamine groups include, but are not limited to, —CH$_2$NH$_2$, —CH$_2$CH$_2$NH$_2$, —CH$_2$CH(CH$_3$)NH$_2$, —CH$_2$CH$_2$CH$_2$CH$_2$NH$_2$, and the like.

In some embodiments, the $C_{n-m}$ alkylamine is covalently bonded, for example, to a ligand described herein. In some embodiments, the $C_{n-m}$ alkylamine is covalently bonded, for example, to a ligand described herein via the nitrogen atom of the alkylamine group (i.e., —($C_{n-m}$ alkyl)-(NH)-ligand). Exemplary alkylamine groups covalently bonded to a ligand include, but are not limited to, —CH$_2$NH-ligand, —CH$_2$CH$_2$NH-ligand, —CH$_2$CH(CH$_3$)NH-ligand, —CH$_2$CH$_2$CH$_2$NH-ligand, and the like.

As used herein, the term "ligand" refers to a group capable of ligating (i.e., complexing) to one or more metal ions. Exemplary ligands include, but are not limited to, 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N',N",N'''-tetraacetic acid (TETA), and 1,4,7,10-tetraaza-1,4,7,10-tetra-(2-carbamoyl methyl)-cyclododecane (TCMC).

Methods of Use

The present application further provides a method of treating a cancer in a subject, the method comprising:
i) administering to the subject a therapeutically effective amount of a composition provided herein; and
ii) administering one or more doses of radiation to the subject.

As used herein, the term "subject," refers to any animal, including mammals and invertebrates. For example, mice, rats, other rodents, rabbits, dogs, cats, swine, cattle, sheep, horses, primates, fish, and humans. In some embodiments, the subject is a human. In some embodiments, the subject is a mouse. In some embodiments, the method comprises administering to the subject an effective amount of a composition provided herein. In some embodiments, the methods described herein are in vitro methods. In some embodiments, the methods described herein are in vivo methods.

The present application further provides a method of imaging a cancer in a subject, the method comprising:

i) administering to the subject a therapeutically effective amount of a composition a composition provided herein; and ii) imaging the subject with a suitable imaging technique.

In some embodiments, steps i) and/or ii) are repeated multiple times (e.g., two times, three times, four times, etc.).

The present application further provides a method of treating a cancer in a subject, the method comprising:

i) administering to the subject a therapeutically effective amount of a composition provided herein;

ii) imaging the subject with a suitable imaging technique; and iii) administering one or more doses of radiation to the subject.

In some embodiments, the method further comprises administering an additional therapeutically effective amount of the composition to the subject after step ii) and prior to step iii). In some embodiments, steps i), ii), and/or iii) are repeated multiple times (e.g., two times, three times, four times, etc). In some embodiments, the method further comprises imaging the subject with a suitable imaging technique after step iii).

The present application further provides a method of monitoring treatment of a cancer in a subject, the method comprising:

i) administering to the subject a therapeutically effective amount of a composition provided herein;

ii) imaging the subject with a suitable imaging technique; and iii) administering one or more doses of radiation to the subject.

In some embodiments, the method further comprises administering an additional therapeutically effective amount of the composition to the subject after step ii) and prior to step iii). In some embodiments, steps i), ii), and/or iii) are repeated multiple times (e.g., two times, three times, four times, etc.). In some embodiments, the method further comprises imaging the subject with a suitable imaging technique after step iii).

In some embodiments, the subject has been identified and/or diagnosed as having the cancer to be treated prior to performing one or more of the methods described herein. In some embodiments, the subject is identified and/or diagnosed as having the cancer to be treated after the imaging step of one or more of the methods described herein.

In some embodiments, the composition provided herein radiosensitizes the cancer (e.g., upon administration to the subject and contact with the cancer). As used herein, the term "radiosensitize" would be readily understood by one of ordinary skill in the art and generally refers to the process of increasing the sensitivity of the cancer cells to radiation therapy (e.g., photon radiation, electron radiation, proton radiation, heavy ion radiation, and the like).

In some embodiments, the cancer is a solid tumor. In some embodiments, the cancer is selected from the group consisting of lung cancer, brain cancer, cancer of the head and neck, cervical cancer, pancreatic cancer, breast cancer, prostate cancer, liver cancer, colon cancer, endometrial cancer, bladder cancer, skin cancer (e.g., melanoma), renal cancer, and gastric cancer. In some embodiments, the cancer is a metastatic cancer.

In some embodiments, the suitable imaging technique is a non-invasive imaging technique. In some embodiments, the suitable imaging technique is a minimally invasive imaging technique. As used herein, the term "minimally invasive imaging technique" comprises imaging techniques employing the use of an internal probe or injection of the composition provided herein via syringe. Example imaging techniques include, but are not limited to, magnetic resonance imaging (MRI), tomographic imaging, positron emission tomography (PET) imaging, single-photon emission computed tomography (SPECT) imaging, PET with computed tomography (CT) imaging, and PET-MRI imaging. In some embodiments, the imaging is performed using magnetic resonance imaging, computed tomography imaging, positron emission tomography imaging, or any combination thereof.

In some embodiments, the methods provided herein further comprise waiting a time sufficient to allow the composition to accumulate at a cell or tissue site (e.g., a cell or tissue site in a subject) associated with the cancer, prior to imaging. In some embodiments, the methods provided herein further comprise waiting a time sufficient to allow the composition to accumulate at a cell or tissue site (e.g., a cell or tissue site in a subject) associated with the cancer, prior to administering the dose of radiation to the subject. In some embodiments, the methods provided herein further comprise waiting a time sufficient to allow the composition to accumulate at a cell or tissue site (e.g., a cell or tissue site in a subject) associated with the cancer, prior to administering the dose of radiation to the subject and/or imaging the subject.

In some embodiments, the time sufficient to allow the composition to accumulate at a cell or tissue site is from about 30 seconds to about 24 hours, for example, about 30 seconds to about 24 hours, about 30 seconds to about 12 hours, about 30 seconds to about 6 hours, about 30 seconds to about 2 hours, about 30 seconds to about 1 hour, about 30 seconds to about 30 minutes, about 30 seconds to about 10 minutes, about 10 minutes to about 24 hours, about 10 minutes to about 12 hours, about 10 minutes to about 6 hours, about 10 minutes to about 2 hours, about 10 minutes to about 1 hour, about 10 minutes to about 30 minutes, about 30 minutes to about 24 hours, about 30 minutes to about 12 hours, about 30 minutes to about 6 hours, about 30 minutes to about 2 hours, about 30 minutes to about 1 hour, about 1 hour to about 24 hours, about 1 hour to about 12 hours, about 1 hour to about 6 hours, about 1 hour to about 2 hours, about 2 hours to about 24 hours, about 2 hours to about 12 hours, about 2 hours to about 6 hours, about 6 hours to about 24 hours, about 6 hours to about 12 hours, or about 12 hours to about 24 hours.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

When employed in methods of treating a disease, the compounds provided herein can be administered in combination with one or more additional therapeutic agents provided herein. Exemplary additional therapeutic agents include, but are not limited to, chemotherapeutic agents, immunotherapeutic agents, and anesthetic agents (e.g., for use in combination with a surgical procedure).

In some embodiments, the additional therapeutic agent is a chemotherapeutic agent. Exemplary chemotherapeutic agents include, but are not limited to, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib, imatinib, gemcitabine, uracil mustard, chlormethine, ifosfamide, melphalan, chlorambucil, pipobroman, triethylenemelamine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide.

In some embodiments, the additional therapeutic agent is an immunotherapeutic agent. Exemplary immunotherapeutic agents include, but are not limited to, alemtuzumab, atezolizumab, ipilimumab, ofatumumab, nivolumab, pembrolizumab, rituximab, durvalumab, human type I interferon-α (i.e. IFN-α), and interleukin-2.

In some embodiments, the additional therapeutic agent is an anesthetic agent. Exemplary anesthetic agents include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the additional therapeutic agent is administered simultaneously with a composition provided herein. In some embodiments, the additional therapeutic agent is administered after administration of the composition provided herein. In some embodiments, the additional therapeutic agent is administered prior to administration of the composition herein. In some embodiments, the composition provided herein is administered during a surgical procedure. In some embodiments, the composition provided herein is administered in combination with an additional therapeutic agent during a surgical procedure.

The additional therapeutic agents provided herein can be effective over a wide dosage range and are generally administered in an effective amount. It will be understood, however, that the amount of the therapeutic agent actually administered will usually be determined by a physician, according to the relevant circumstances, including the condition to be imaged, the chosen route of administration, the actual compound administered, the age, weight, and response of the individual subject, the severity of the subject's symptoms, and the like.

Pharmaceutical Formulations

When employed as pharmaceuticals, the compositions and therapeutic agents provided herein can be administered in the form of pharmaceutical formulations. These formulations can be prepared as described herein or elsewhere, and can be administered by a variety of routes, depending upon whether local or systemic treatment is desired and upon the area to be treated. In some embodiments, the administration is selected from the group consisting of pulmonary administration (e.g., by inhalation or insufflation of powders or aerosols, including by nebulizer, intratracheal administration, or intranasal administration), oral administration, or parenteral administration (e.g., intravenous, intraarterial, subcutaneous, intraperitoneal, intramuscular or injection or infusion, intracranial, intrathecal, intraventricular administration, and the like). In some embodiments, the administration is intravenous or nasal administration.

Parenteral administration can be in the form of a single bolus dose, or may be, for example, by a continuous perfusion pump. Conventional pharmaceutical carriers, aqueous, powder, or oily bases, thickeners and the like, may be necessary or desirable.

Also provided are pharmaceutical formulations which contain, as the active ingredient, a composition provided herein in combination with one or more pharmaceutically acceptable carriers (excipients). In making a pharmaceutical formulation provided herein, the nanoparticle composition may be, for example, mixed with an excipient or diluted by an excipient. When the excipient serves as a diluent, it can be a solid, semi-solid, or liquid material, which acts as a vehicle, carrier, or medium for the nanoparticle composition. Thus, the pharmaceutical formulations can be in the form of powders, lozenges, elixirs, suspensions, emulsions, solutions, syrups, aerosols (as a solid or in a liquid medium), sterile injectable solutions, sterile packaged powders, and the like.

EXAMPLES

General Methods and Materials

Sodium hydroxide (NaOH, 99.99%), hydrochloric acid (HCl, 36.5-38%), dimethylsulfoxide (DMSO, >99.5%) and $BiCl_3$ (>98%) were purchased from Aldrich Chemical (France). Acetonitrile ($CH_3CN$, >99.9%) was purchased from Carlo Erba (France). Trifluoroacetic acid (TFA, >99%) was purchased from Alfa Aesar (United Kingdom). Copper sulfate pentahydrate ($CuSO_4.5H_2O$, 98%) was purchased from Merck (Germany). Gd and Bi (1000 mg/mL±0.2%) ICP single element standard solution were purchased from Carl Roth (Germany). SiGd nanoparticles (SiGdNP) were purchased from Nano-H (France). The derivative DOTA chelate (2,2',2"-(10-(2-((2,5-dioxopyrrolidin-1-yl)oxy)-2-oxoethyl)-1,4,7,10-tetraazacyclododecane-1,4,7-triyl)triacetic acid) was purchased from ChemaTech (France). All products were used without further purification. Only Mili-Q water (ρ>18 MΩ·cm) was used for the aqueous solution preparation. Elementary analysis or particles were performed by the Filab company (France).

Example 1. Preparation of SiBiGd Nanoparticles (SiBiGdNP)

Step 1. Synthesis of SiGd Nanoparticles (SiGdNP)

After the formation of a gadolinium oxide core $Gd_2O_3$ in diethylene glycol (see e.g., Bridot et al., *J. Am. Chem. Soc.*, 2007, 129:5047), a polysiloxane shell was grown using hydrolysis-condensation of tetraethyl orthosilicate (TEOS) and aminopropyl triethoxysilane (APTES) to form a SiGd nanoparticle.

Step 2. Synthesis of SiGdNP-DOTA Nanoparticles

1033 µmol of SiGd nanoparticles (SiGdNP) were dispersed in 12.7 mL of water for 1 hour at a pH of 7.4 ($[Gd^{3+}]$=81 mM). Then 15 mL of water were added. 591 mg of the derivative DOTA chelate (776 µmol; ratio Gd/DOTA=1.3) were dissolved in 2.36 mL of DMSO ([DOTA]=250 mg/mL). This solution was then gradually added to the SiGdNP solution under stirring at room temperature and the pH adjusted to 7.4 by addition of NaOH solution. The particles solution was stirred for 5 h. The mixture was diluted in water to $[Gd^{3+}]$=22.5 mM (V=59 mL) in order to have a solution containing less than 4% DMSO and the pH was decreased to 1 to avoid ionic interactions between ammonium of SiGdNP and carboxylate of DOTA-NHS. Particles were then purified by tangential filtration trough Vivaspin® membranes (MWCO=5 kDa) purchased from Sartorius Stedim Biotech (France). The colloidal solution was introduced into Vivaspin® tubes and centrifuged. This step was repeated several times, by filling the tubes with water and centrifuging again, until the desired purification rate was reached (×26,000). The particles solution was concentrated to approximately $[Gd^{3+}]$=100 mM, the pH adjusted to 7.4 and finally the solution was sterile filtered through a 0.2 µm syringe filter in order to remove the largest impurities. It was freeze-dried for storage, using a Christ Alpha 1-2 lyophilizer. The Gd yield for the synthesis was 41%.

Step 3. SiBiGdNP Synthesis

The SiGdNP-DOTA particles were dispersed in 6.5 mL of water for 1 hour at a pH of 7.4 ([Free DOTA]=46 mM, 1 equivalent, $n_{free\ DOTA}$=302 µmol). A solution of $Bi^{3+}$ at 250 mM was prepared by dissolving $BiCl_3$ in HCl 6M. This solution was then added slowly to the nanoparticles under stirring at 50° C. (0.3 equivalent, 90.6 µmol) with a pH=6. This step was repeated twice to achieve a total amount of 0.9 equivalent of $Bi^{3+}$ (271.8 µmol). The solution was stirred overnight at room temperature. The mixture was diluted in water ([Free DOTA]=20 mM, V=15 mL). Particles were purified by tangential filtration trough Vivaspin® membranes (MWCO=50 kDa) to remove the free bismuth hydroxide. The colloidal solution was introduced into Vivaspin® tubes, and centrifuged. The filtered solution was recovered and purified by tangential filtration with Vivaspin® membranes (MWCO=5 kDa) to remove the degradation products. The particles solution was concentrated to approximately $[Gd^{3+}]$=100 mM and finally the solution was filtered through a 0.2 µm syringe filter. SiBiGdNP were freeze-dried for storage, using a Christ Alpha 1-2 lyophilizer. The Gd yield for the synthesis was 67%.

Figure 6A:
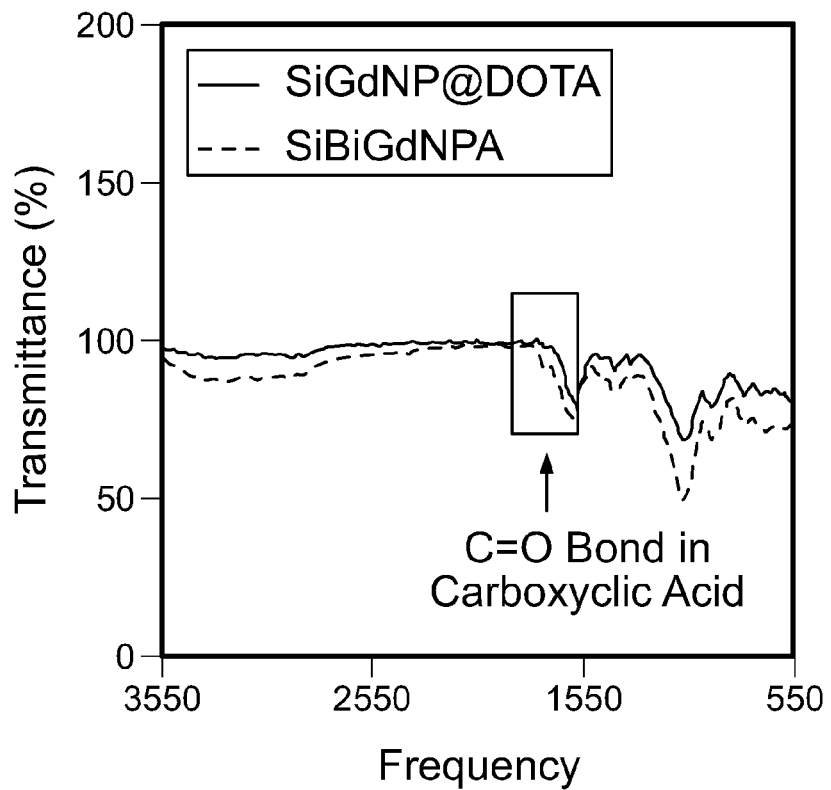
FIG. 6A shows results of infrared spectrum measurements of complexation of $Bi^{3+}$ atoms in SiBiGdNP.
Figure 6B:
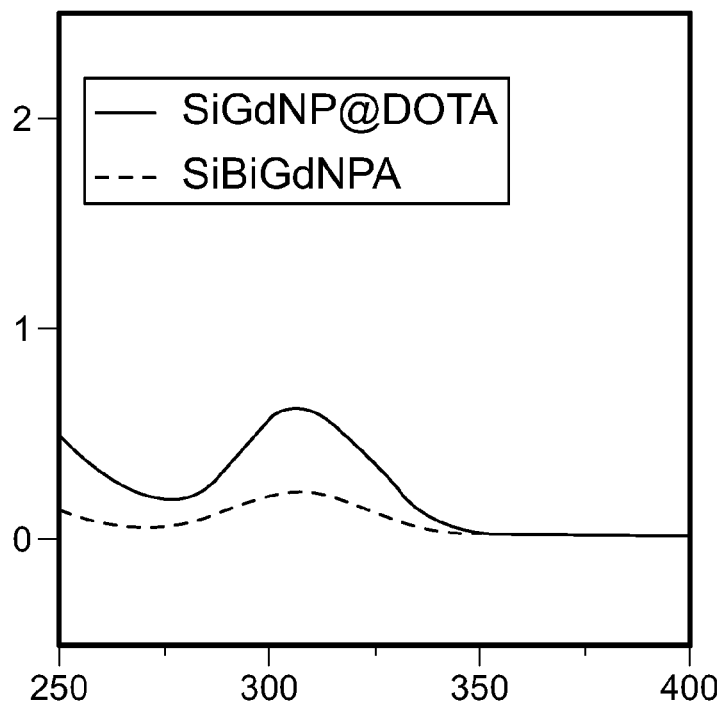
FIG. 6B shows results of absorbance measurements of complexation of $Bi^{3+}$ atoms in SiBiGdNP.

Preparation of the silica-based bismuth-gadolinium nanoparticles provided herein (SiBiGdNP) were prepared based on a top-down process, for example, as shown in FIG. 1B. As described below, this process can be used to prepare a polysiloxane core DOTA-Gd complexes. Next, the surface of the polysiloxane network was modified by the grafting of DOTA chelates followed by the complexation of $Bi^{3+}$ ions. The infrared and absorbance spectra confirmed the complexation of the $Bi^{3+}$ by the DOTA on the nanoparticle and are shown in FIGS. 6A-6B. The choice of the DOTA as complex agent was made because of its high stability, as described by its log K values, DOTA-Gd=23.6 and DOTA-Bi=30.3.

Example 2. In Vitro Proof of Concept

Figure 1F:
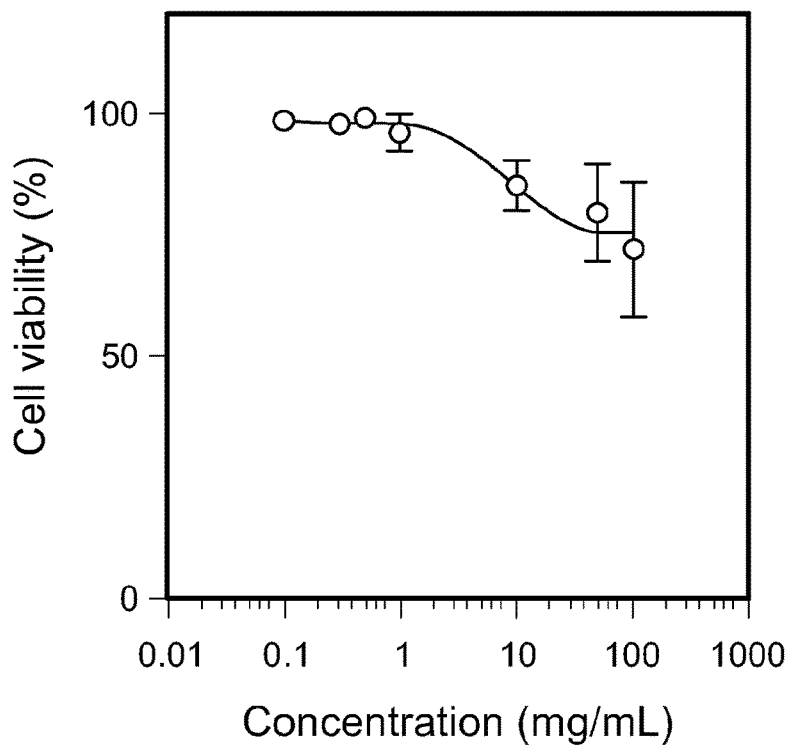
FIG. 1F shows toxicity of the SiBiGdNP as a function of concentration at 72 h post-incubation.
Figure 1G:
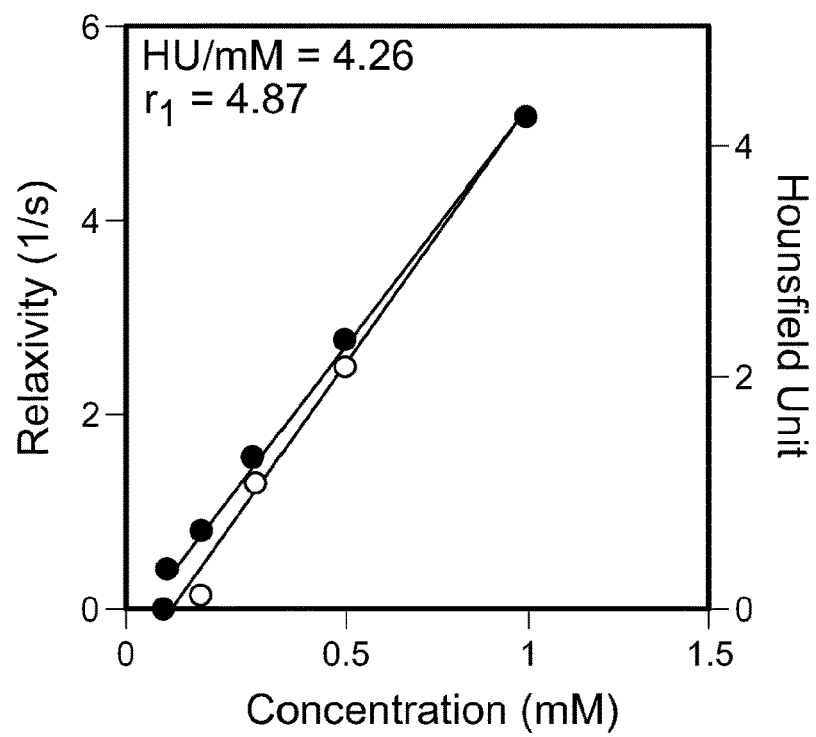
FIG. 1G shows the linear relationship between MRI (relaxivity) and CT (Hounsfield units) and the concentration of nanoparticles (metal) in aqueous solution.

As is described throughout the examples, the hydrodynamic diameter (4.5+/−0.9 nm) of the nanoparticle provided herein is below the 10 nm kidney filtration threshold, as shown in FIG. 1C, thereby minimizing potential off-target side effects (see e.g., Choi et al, *Nat. Biotechnol.* 2007, 25:1165). The zeta potential of the SiBiGdNP at pH=7 is equal to −3.6 mV. The polysiloxane-base of the nanoparticle was covalently bound to an average of ~10 DOTA ligands complexing gadolinium atoms and an average of ~5 DOTA ligands complexed with bismuth atoms, as shown in FIG. 1D. The absorbance measurements demonstrated that less than 5% of free bismuth was released, as shown in FIG. 1E, 48 h postincubation at pH=5 and 7, thereby limiting the toxicity of the nanoparticles. The stability constant value (loK=30.3) confirms the stability of SiBiGdNP (see e.g., Csajbok et al, *Inorg. Chem.* 2003, 42:2342). This was further confirmed by an $IC_{50}$ index equal to 10 mg/mL, a concentration ~30 times higher than the in vivo injected dose (0.32 mg/mL) used in this study, as shown in FIG. 1F. Moreover, the specific structure of the nanoparticle allowed the SiBiGdNP to be imaged in both MR and CT imaging techniques at a concentration as low as 0.1 mg/mL, as shown in FIG. 1G. The SiBiGdNP acted as a $T_1$ positive contrast agent with a longitudinal relaxivity ($r_1$) and a transverse relaxivity ($r_2$) measured, at 7 tesla, to be $r_1$=4.87 $s^{-1} \cdot mM^{-1}$ and $r_1/r_2$=1.46, which is slightly higher than other FDA-approved MR contrast agents (see e.g., Na et al, *Angew. Chem. Int. Ed. Engl.* 2007, 45:5397). The CT contrast induced by the Bi atoms was equal to 4.26 HU $mM^{-1}$, which is in the range of clinically used CT contrast agents (see e.g., Kao et al, *Academic Radiology,* 2003, 10:586).

Figure 2A:
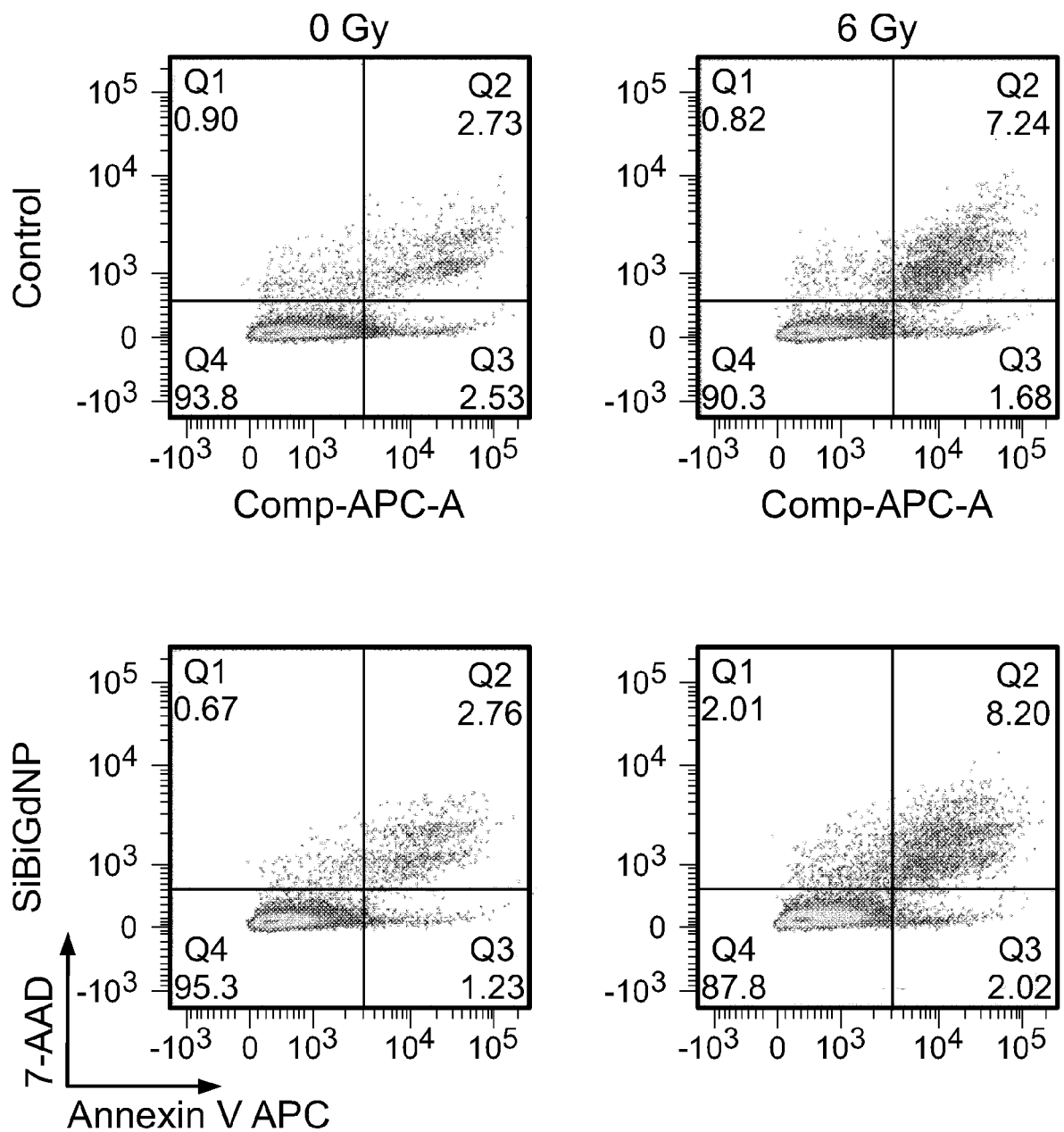
FIG. 2A shows qualitative images representing the quantification of the increase in apoptosis caused by the presence of SiBiGdNP under 6 MV irradiations using flow cytometry.
Figure 2B:
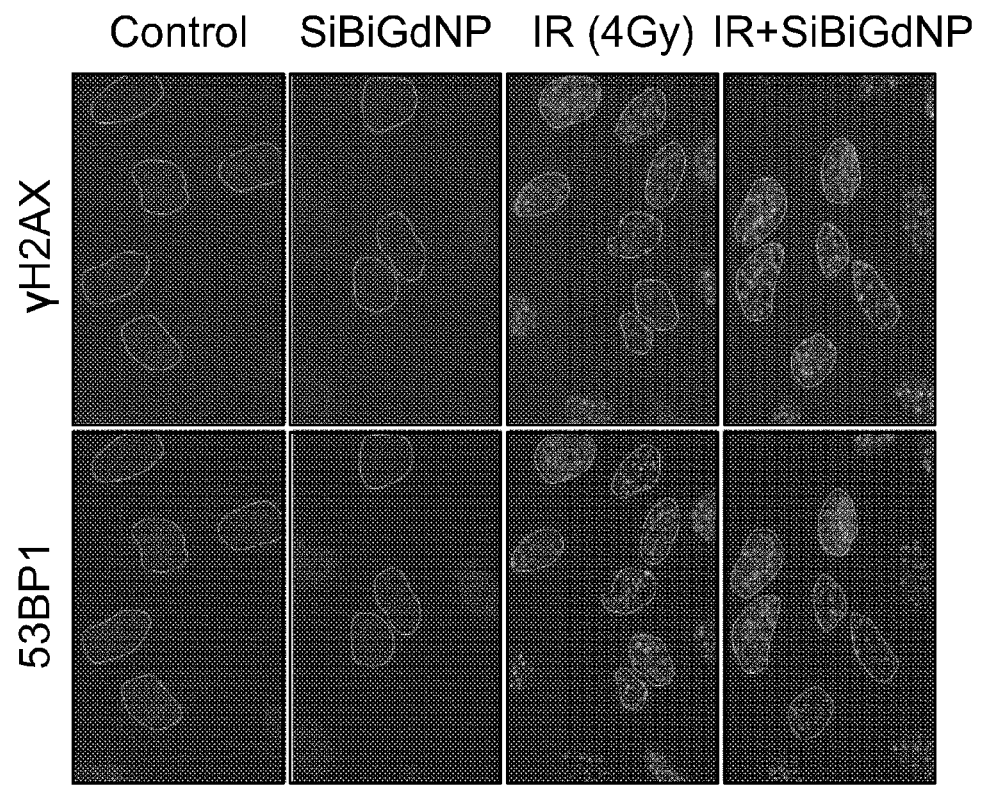
FIG. 2B shows qualitative images representing the amount of γH2AX and 53BP1 foci formation, with and without 4 GY irradiation, with and without nanoparticles, and 15 min post-irradiation.
Figure 2C:
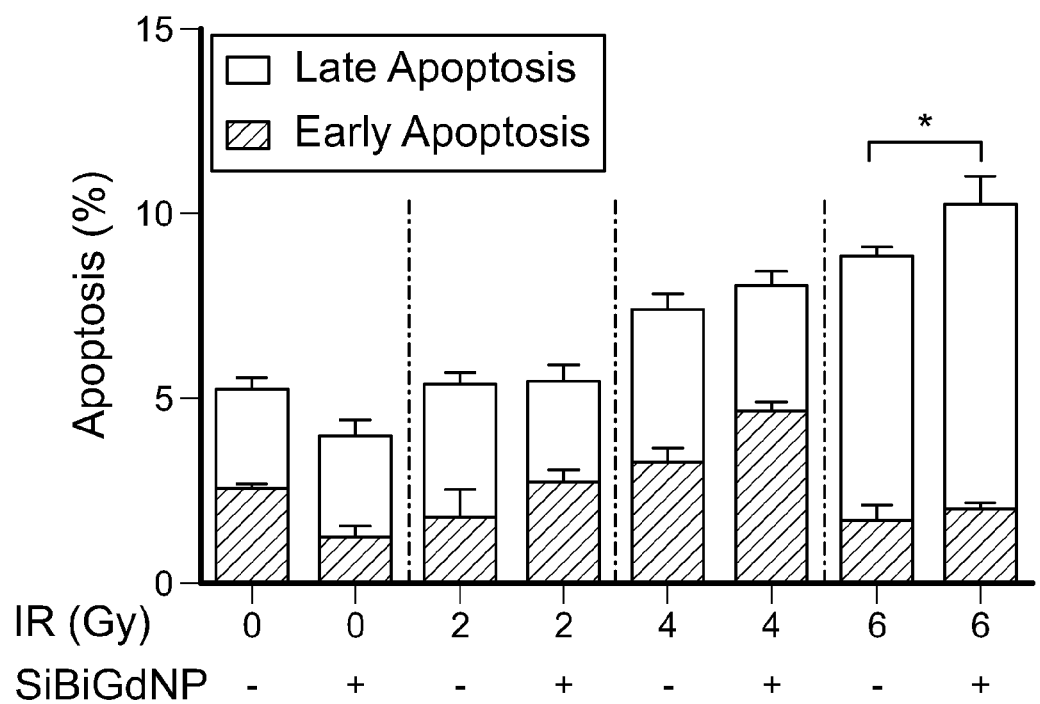
FIG. 2C shows results of a FACS study of early and late apoptosis induced by SiGdNP under external radiation.
Figure 2D:
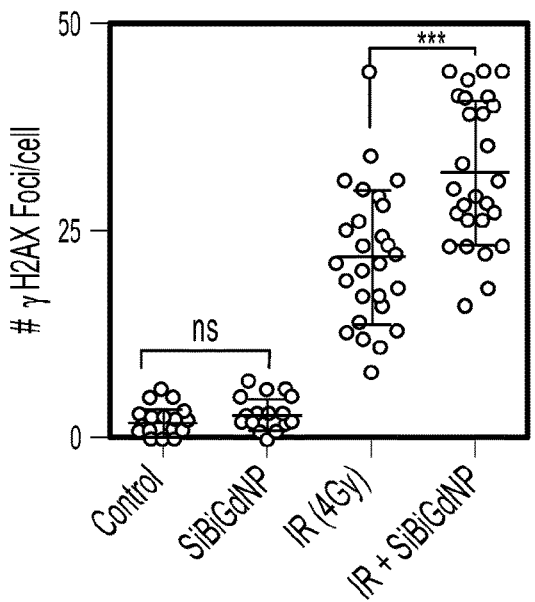
FIG. 2D shows the number of cells with more than 10 γH2AX foci (n=3). All data are represented as a mean±SD. P-values were calculated using two-tailed test * $P<0.05$, * $P<0.001$, ** $P<0.0001$.
Figure 2E:
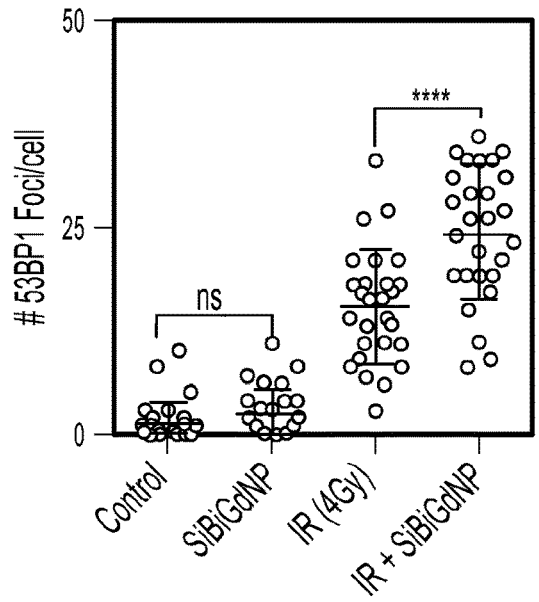
FIG. 2E shows the number of cells with more than 10 53PB1 foci (n=3). All data are represented as a mean±SD. P-values were calculated using two-tailed test * $P<0.05$, * $P<0.001$, ** $P<0.0001$.
Figure 2F:
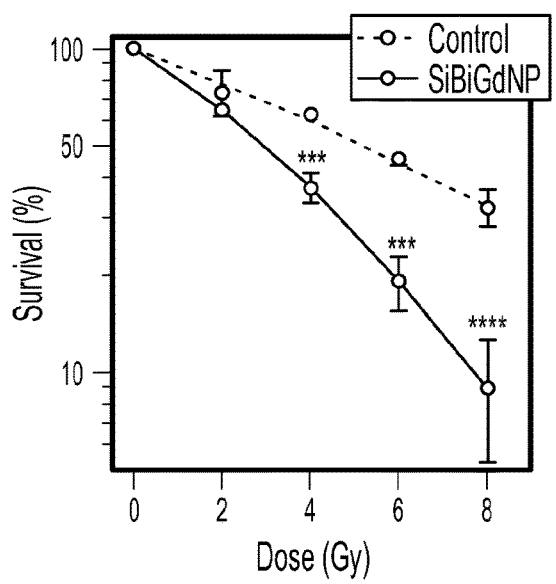
FIG. 2F shows the results of a clonogenic assay (n=3) illustrating the long-term effect induced by the presence of nanoparticles during irradiation. All data are represented as a mean±SD. P-values were calculated using two-tailed test * $P<0.05$, * $P<0.001$, ** $P<0.0001$.
Figure 7:
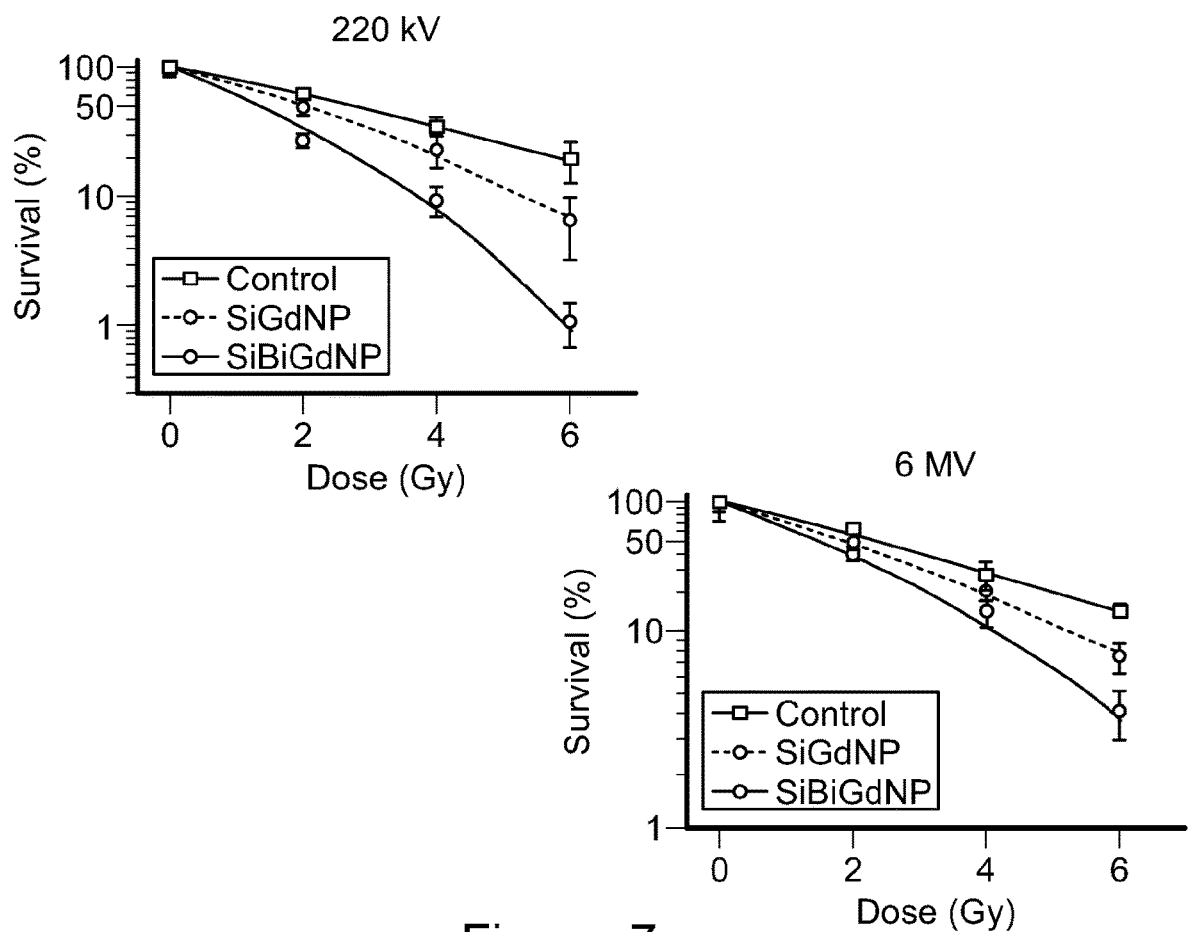
FIG. 7 shows results of a clonogenic assay comparing the efficacy of SiBiGdNP and SiGd nanoparticles (SiGdNP).

Both gadolinium (Z=64) and bismuth (Z=83) produce photoelectrons and Auger electrons after interaction with a clinical 6 MV radiation beam (see e.g., McMahon et al, *Nanoscale,* 2016, 8:581). This local dose amplification was confirmed by an increase in apoptotic cell death and DNA damage, as shown in FIGS. 2A-2B. After 24 hours post-irradiation, a significant increase in apoptosis is observed in presence of radiation and SiBiGdNP (10.2±0.8% vs. 8.9±5%, n=3, p-value=0.047), as shown in FIG. 2C. DNA damage was demonstrated by a significant increase in the presence of γH2AX and 53BP1, as shown in FIGS. 2D-2E (p=0.001 and p<0.0001, respectively). The increase in cell death was confirmed by clonogenic assay, as shown in FIG. 2F (p<0.001 from 4 Gy and above) and FIG. 7 demonstrating a dose enhancement factor of 1.99.

The adjunction of $Bi^{3+}$ atoms in the nanoparticles increased the amount of physical effect, and thus, led to an overall increase of efficacy. This was observed by clonogenic assay on the cell line A549, for both preclinical and clinical radiation beams. This result confirmed the higher efficacy of SiBiGdNP over SiGdNP. Preclinically, the clonogenic assay was performed with the SARRP machine. Clinically, the cells were irradiated with a 6 MV Varian Truebeam® machine. Cells were irradiated following an established measurement protocol (see e.g., Detappe et al, *Cancer Nanotechnol.* 2015, 6:4).

Example 3. In Vivo Theranostic Applications

Figure 3A:
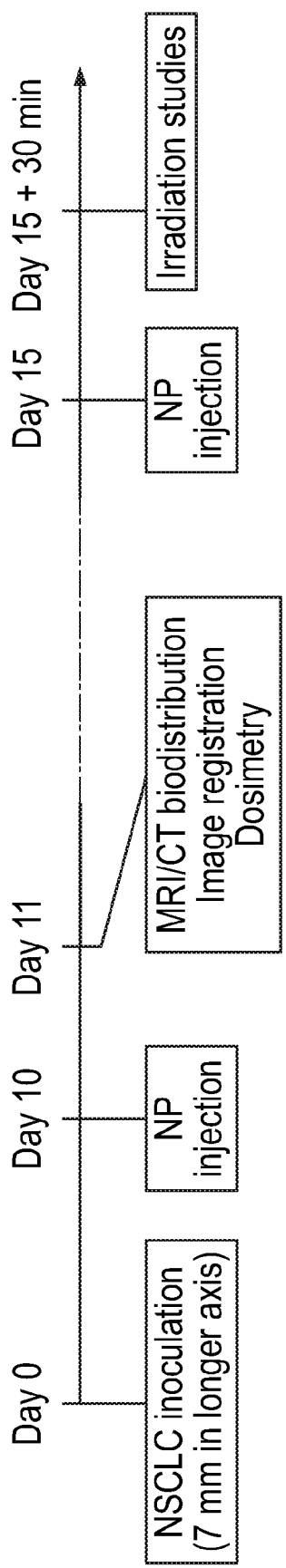
FIG. 3A shows an experimental timeline based on a current clinical workflow for MR-guided radiation therapy.
Figure 3B:
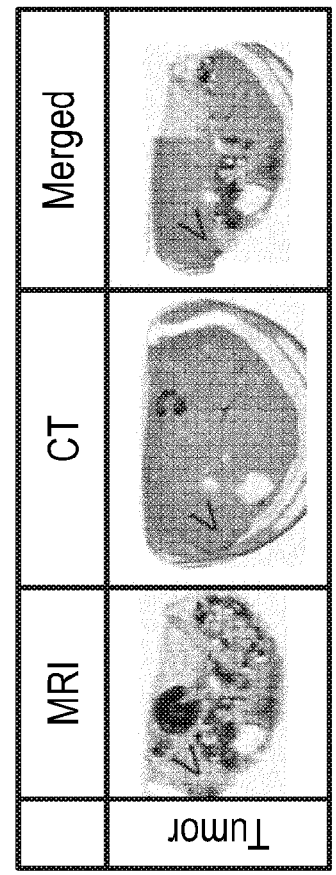
FIG. 3B shows fusion of the CT and MRI acquisition to improve the accuracy of the tumor imaging. Yellow arrows show the contrast emitted by the Gd and Bi in the tumor.

To demonstrate in vivo efficacy, a fast-growing subcutaneous xenograft solid tumor model (A549 lung adenocarcinoma) was passively targeted with SiBiGdNP. In vivo experiments were performed to mimic actual clinical workflow, as shown in FIG. 3A. The pharmacokinetics of the SiBiGdNP was carried out in blood samples over 24 h while the biodistribution of the nanoparticles was assessed at 15 min, 3 h, 6 h, and 24 h post-injection by MRI and CT acquisitions, as shown in FIGS. 3B-3D and FIG. 8.

Biodistribution Assay

Animals were injected with 0.42 mg/g of SiBiGdNP and imaged by MRI (1.5T) then μCT. Yellow arrows show the contrast observed in the tumor induced by the Bi atoms for the CT scans, and by the Gd atoms for the MRI scans. For the MRI study, an ASpect One-Touch MRI with a 1.5 Tesla magnetic field was used. A $T_1$ gradient echo sequence was used to track and quantify the amount of nanoparticles in the different organs. More specifically, a whole body acquisition with the following parameters were used: echo time of 4 ms, repetition time of 30 ms, flip angle of 57 degrees, slice thickness of 0.5 mm. For the μCT acquisition, a nanoScan PET/CT Mediso scanner was used. The acquisition parameters were: 45 kVp, exposure time of 1100 ms, resolution of 12.8 pixels per mm, slice thickness of 0.08 mm. For both imaging techniques, a calibration curve was performed to convert respectively the $T_1$ value and the Hounsfield unit to a dose in mg/mL of nanoparticles. Each animal was anesthetized continuously with isoflurane during the imaging sessions. Reference scans were performed before IV injection of the SiBiGdNP by imaging with MRI, followed by CT scan, using the same bench without moving the animal position. The same experiment was performed at 30 min, 3 h, 6 h, and 24 h post injection. This biodistribution study was then validated with an inductively coupled plasma mass spectrometry (ICP-MS) measurement for each of the time points, with 3 mice per time point. The correlation between the biodistribution of gadolinium and bismuth in the different organs is evidence of the high stability of the nanoparticles.

Figure 3C:
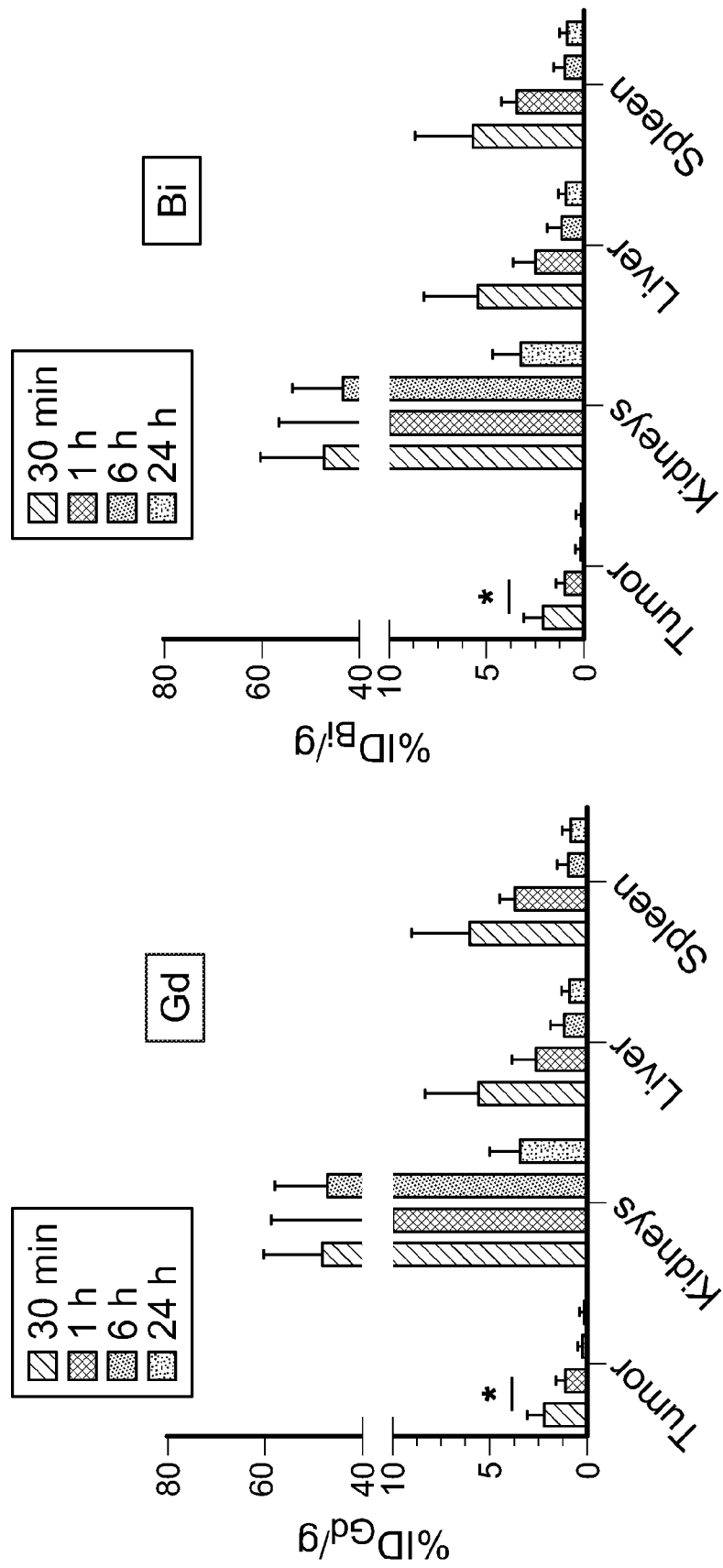
FIG. 3C shows the results of a biodistribution study performed by ICP-MS in 6 animals/time point after i.v. injection of 0.42 mg/g of SiBiGdNP. Quantification was performed to determine the amount of gadolinium (Gd) and bismuth (Bi) as a function of the injected dose of atoms per nanoparticle. *$P<0.05$.
Figure 3D:
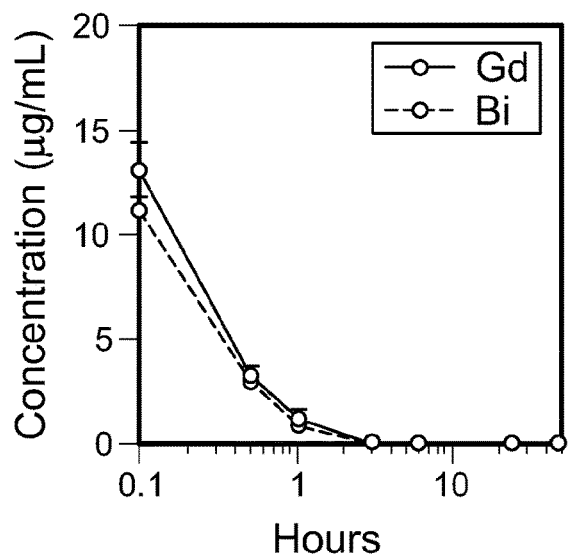
FIG. 3D shows the results of a pharmacokinetic study (n=5) of a SiBiGdNP in blood samples.
Figure 8:
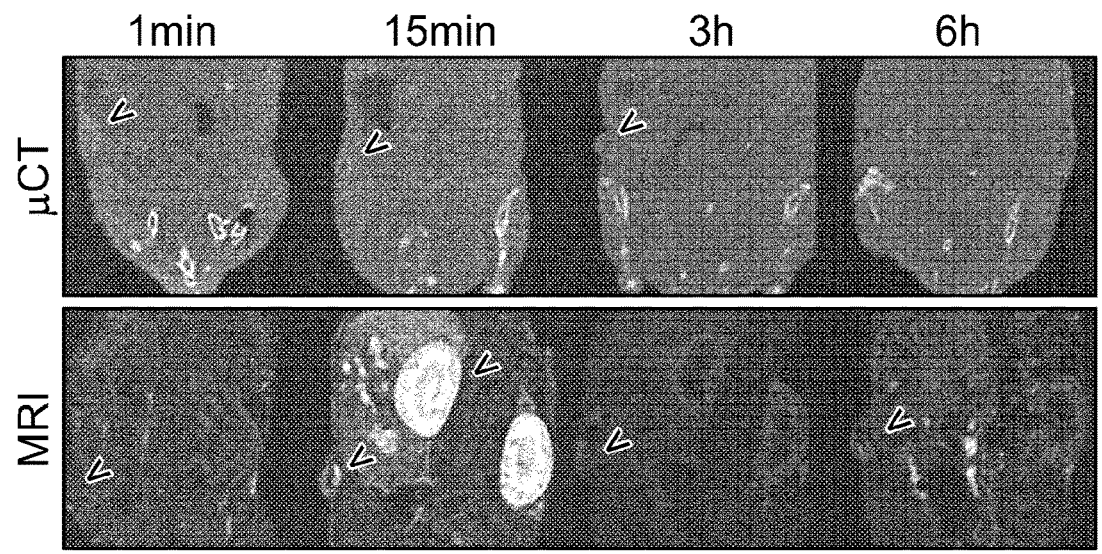
FIG. 8 shows results of magnetic resonance and computed tomography imaging conducted to non-invasively follow biodistribution of the SiBiGdNP.

Due to the tumor's fast growth and its poor vascularization, nanoparticles were still visible 6 h post-injection with 0.49% ID in the tumor, as shown in FIG. 8. Accumulation was observed in kidneys, liver, and spleen, as shown in FIG. 3C, with rapid clearance, expected by the small size of the nanoparticles. Only 0.39% ID of the SiBiGdNP remained in the blood after 24 h, as shown in FIG. 3D, and no organs except the kidneys had more than 2% ID 6 h post-injection, as shown in FIG. 3C.

Dosimetry Study

An irradiation treatment plan was performed using Eclipse (Varian Medical Systems, Inc.) to calculate the dose distribution in the animal. Animals were placed on the top of 10 cm of solid water to mimic the depth in tissue of a typical tumor in the human body. On top of the tumor, 2 cm of tissue equivalent density material was used to create backscatter. The irradiations were performed using a TrueBeam® linear accelerator (Varian Medical Systems, Inc.) with the 6 MV energy mode that is routinely used in the clinic. The radiation beam was targeted only on the tumor. The field size was equal to a 5.5 cm size in the X direction ($X_1$=0.5 cm, $X_2$=5 cm) and 10 cm in the Y direction ($Y_1$=$Y_2$=5 cm). The linear accelerator's primary collimators shielded the body of the mouse.

Figure 3E:
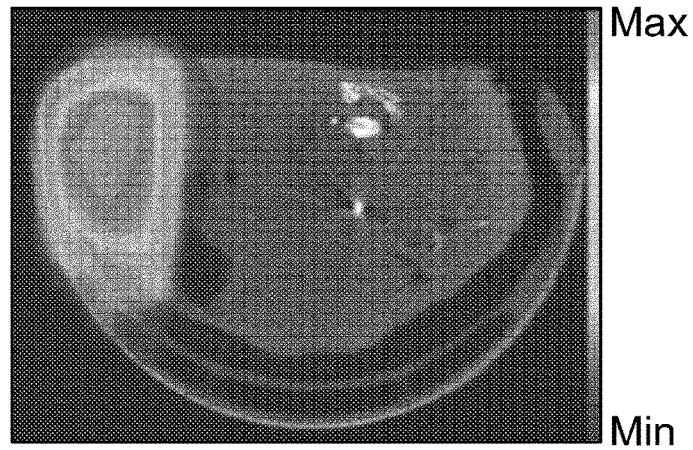
FIG. 3E shows the results of a dosimetry study performed for a single fraction of 10 Gy irradiation delivered from a clinical linear accelerator (6 MV).
Figure 3F:
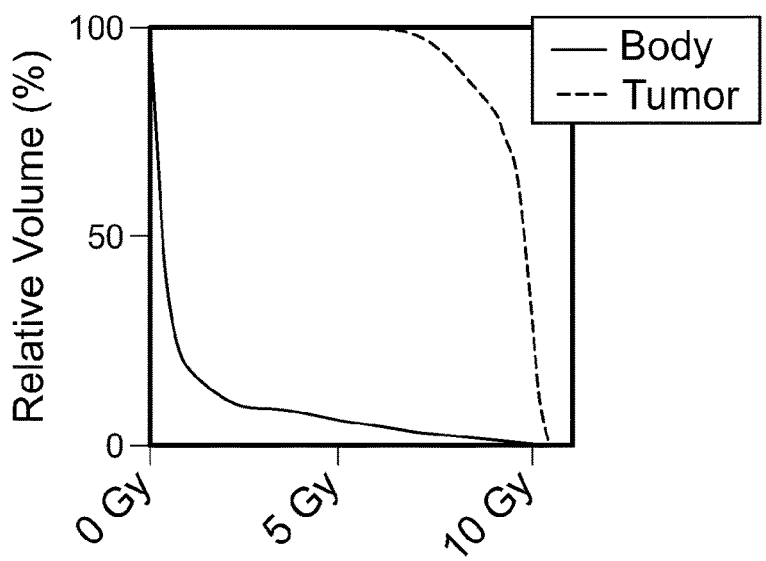
FIG. 3F shows the results of a dose-volume histogram showing the radiation dose distribution in the tumor and in the rest of the body.

A radiation dosimetry study was performed based on an MR-guided radiation therapy clinical workflow. Organs were segmented on the MR images and then merged to the CT scan (FIG. 3B) to calculate the radiation dose distribution, as is performed in the clinic for some procedures (FIGS. 3E-3F). Clinical treatment planning and radiation dose calculation software was used to simulate a single fraction of 10 Gy delivered by a clinical linear accelerator (6 MV photon beam).

Figure 4A:
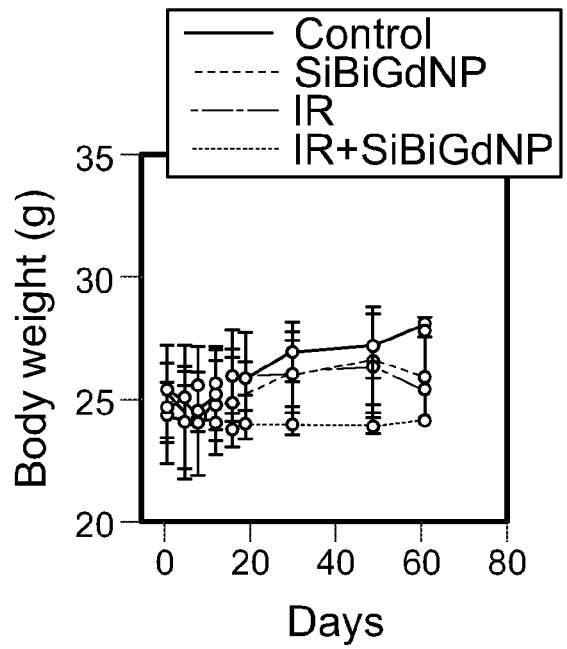
FIG. 4A shows the results of body weight measurements that demonstrate no gross toxicity.
Figure 4C:
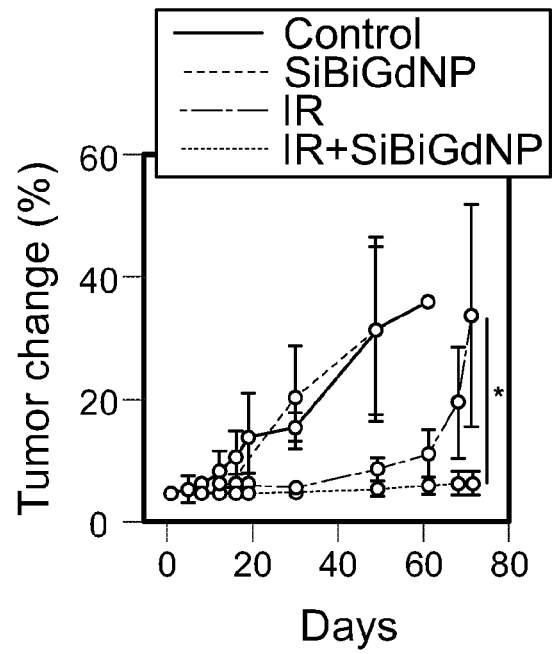
FIG. 4C shows mean tumor size volume of each group (n=5/group).
Figure 4B:
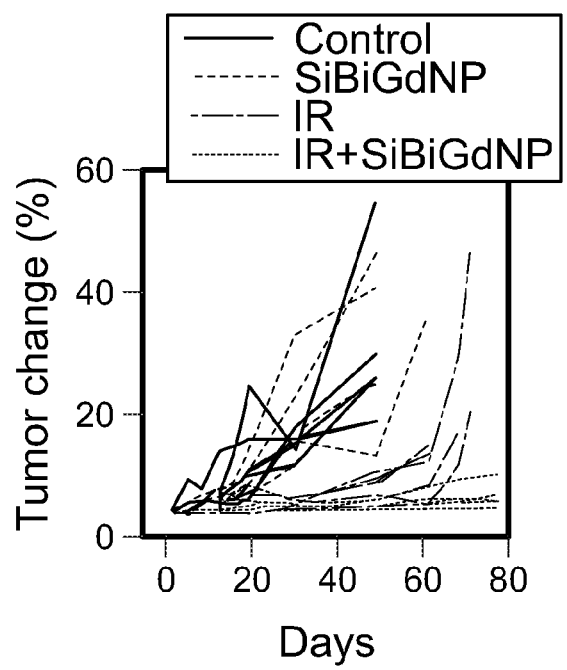
FIG. 4B shows a spider plot of the tumor size evolution as a function of time.
Figure 4D:
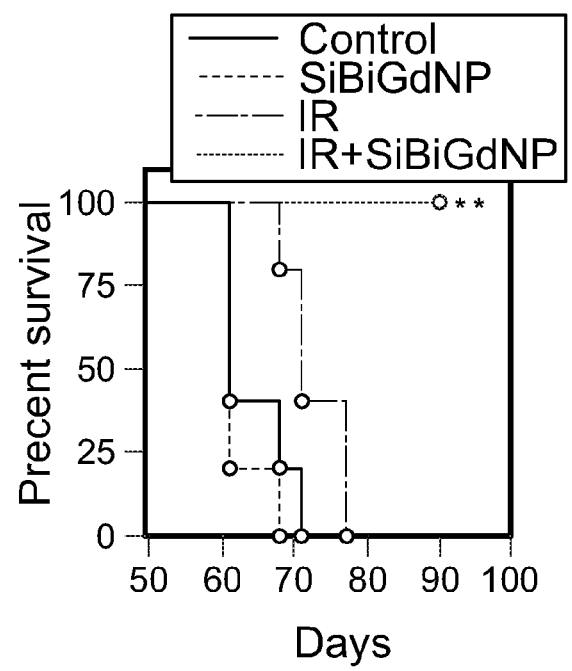
FIG. 4D shows overall survival of each treatment cohort (n=5/group). All data are represented as a mean±SD.* $P<0.05$, ** $P<0.01$.

Therapeutic efficacy was studied with four groups of five mice each divided into two treatment and two control groups. The radiation therapy was performed at the maximum uptake of the nanoparticles in the tumor observed from the MR/CT scans with a clinical 6 MV linear accelerator. This maximum was found to be 30 min post-injection (3.54% ID) and is similar to that of a previous study (see e.g., Detappe et al, *J. Control Release*, 2016, 238:103) conducted with similar nanoparticle size and using the same targeting approach (FIG. 3C and FIG. 8). Body-weight was monitored post-irradiation as one assessment of the safety of the treatment, as shown in FIG. 4A. To examine the long-term efficacy, a tumor growth (FIGS. 4B-4C) and survival (FIG. 4D) studies were performed. Both control groups showed a rapid progression of the tumor burden. Mice treated with 10 Gy irradiation only (no nanoparticles) showed a limited response during the first month followed by rapid tumor growth. The group treated with SiBiGdNP showed statistically significant improvement in tumor growth delay (p=0.045), as shown in FIGS. 4B-4C, and survival compared to the irradiation control group (p=0.0059), as shown in FIG. 4D.

DNA Double Strand Breaks

A549 NSCLC cells were incubated 30 min with SiBiGdNP at a concentration of 0.5 mM and then irradiated. Cells were fixed in 4% paraformaldehyde in PBS at room temperature for 15 min. After fixation, cells were blocked in 1% BSA, 10% FBS, 0.3% triton X-100 in PBS. Next, cells were stained with anti-γH2AX antibody (Millipore) and anti-53BP1 (Santa Cruz) overnight. Subsequently, cells were incubated with secondary anti-mouse-AlexaFluor-594-conjugated IgG and anti-rabbit-AlexaFluor-488-conjugated IgG (Abcam) respectively for the noted primary antibodies. A semi-quantitative analysis was performed to evaluate the number of foci per cell expressing the γH2Ax and 53BP1 markers. Images were visualized with an upright Carl Zeiss microscope with an HXP 120 C light source and a 63×/1.4 oil plan-apochromat objective. Foci were identified in the images and their signal intensity was quantified using CellProfiler cell imaging software (v.2.1.1) (see e.g., Carpenter et al, *Genome Biology*, 2006, 7:R100.

Figure 5A:
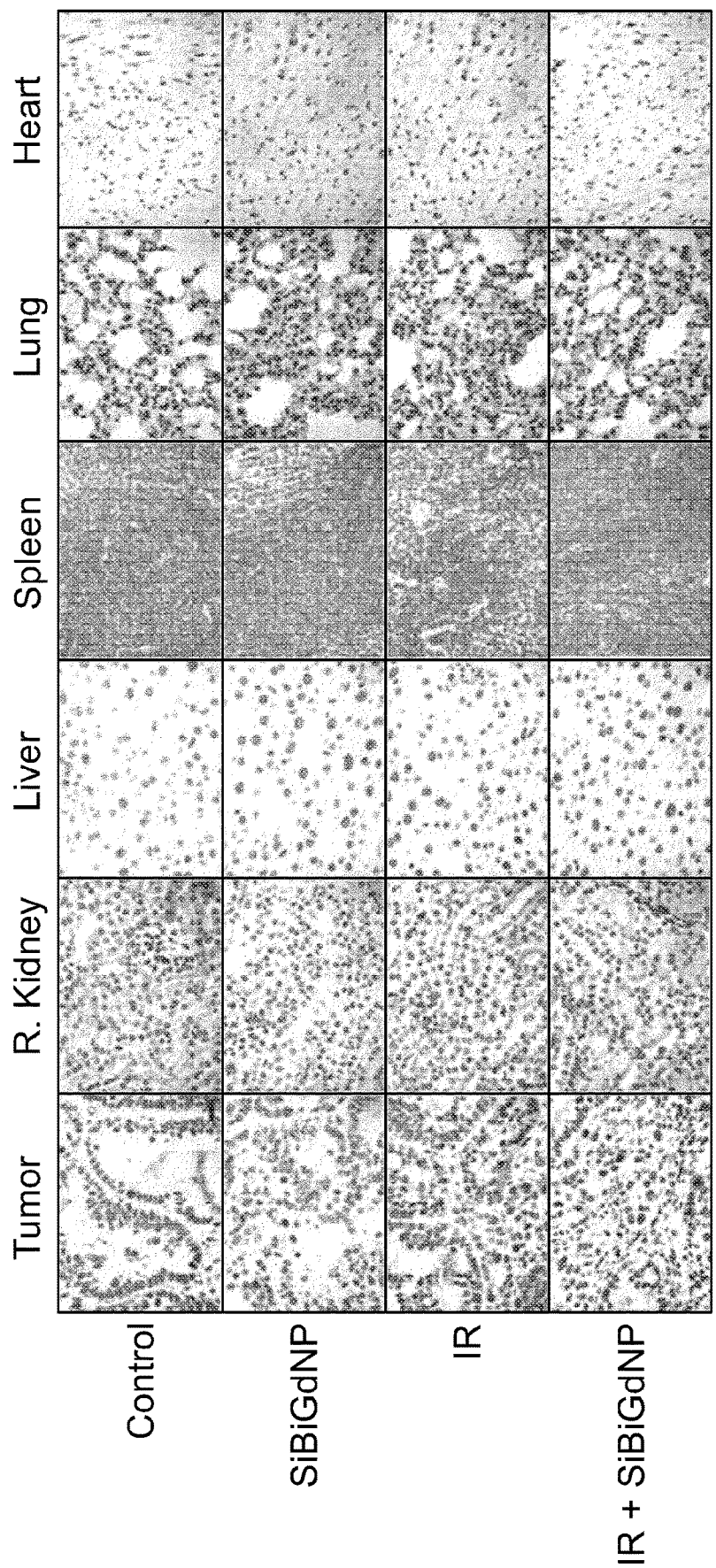
FIG. 5A shows images of γH2AX staining representing the breakage of DNA double strand induced by radiation therapy in a tumor and healthy organs. The damaged cells are brown and the viable cells are blue. Magnification 63×, scale bar=20 µm.
Figure 5B:
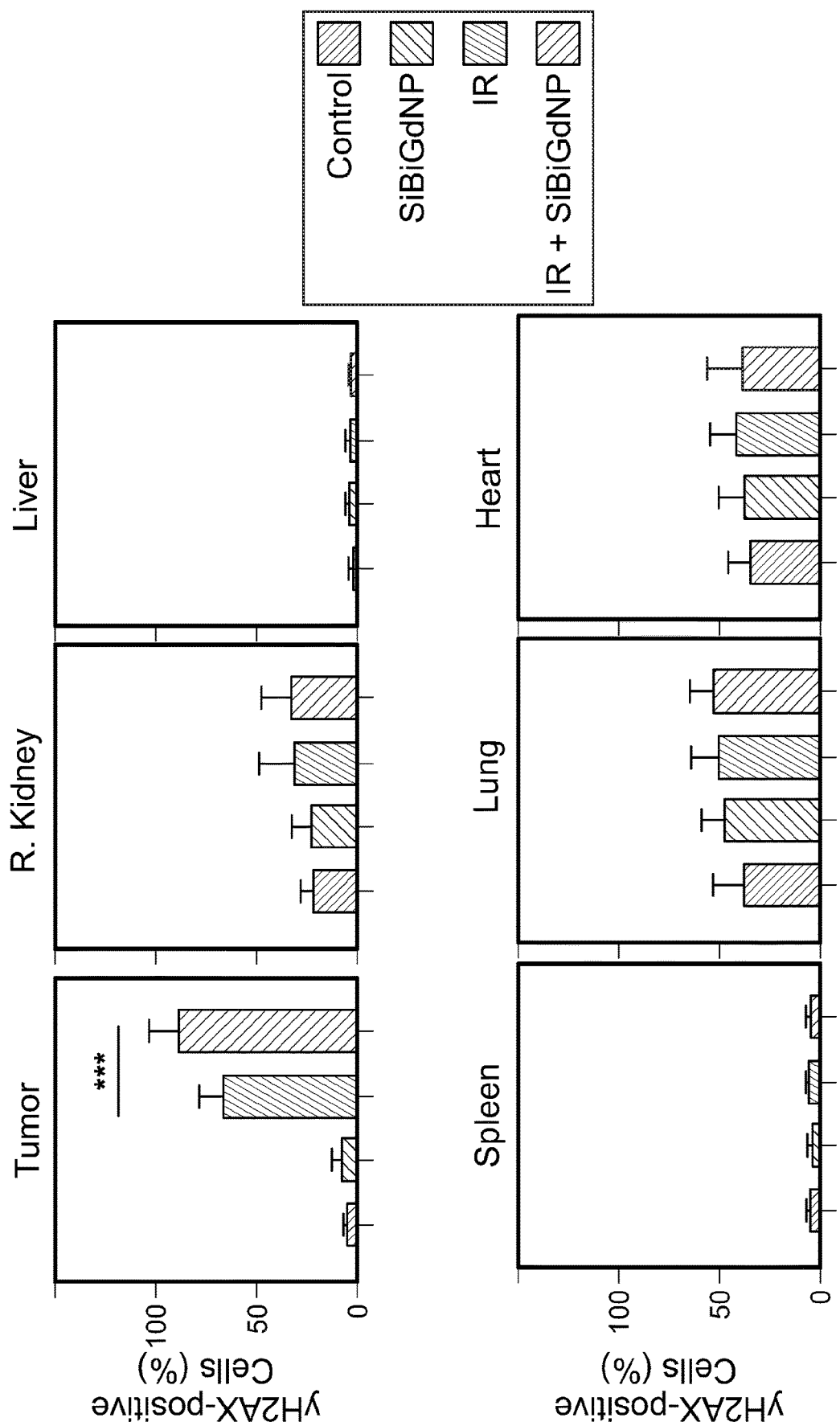
FIG. 5B shows the percent of positive γH2AX cells quantified across n=30 images randomly chosen (n=3/group). Data are shown as mean±STD. *** $P<0.001$.

The precision of the treatment and off-target activation of the nanoparticles was assessed by DNA double strand breaks quantification, as shown in FIG. 5A, 30 min post-irradiation (see e.g., Herter-Sprie et al, *Nat. Commun.* 2014, 5:5870). In the healthy tissue, a non-significant increase of DNA double-strand breaks was observed for the irradiated groups compared to both control (non-irradiated) groups. On the contrary, in the tumor, an increase of DNA damage was observed with the in vivo γH2AX staining when the irradiation is performed with (89.33±14.3%) and without SiBiGdNP (67.31±11.36%) compared to the control groups (8.1±4.3% and 5±1.3% respectively), as shown in FIG. 5B.

H&E Staining

Figure 9:
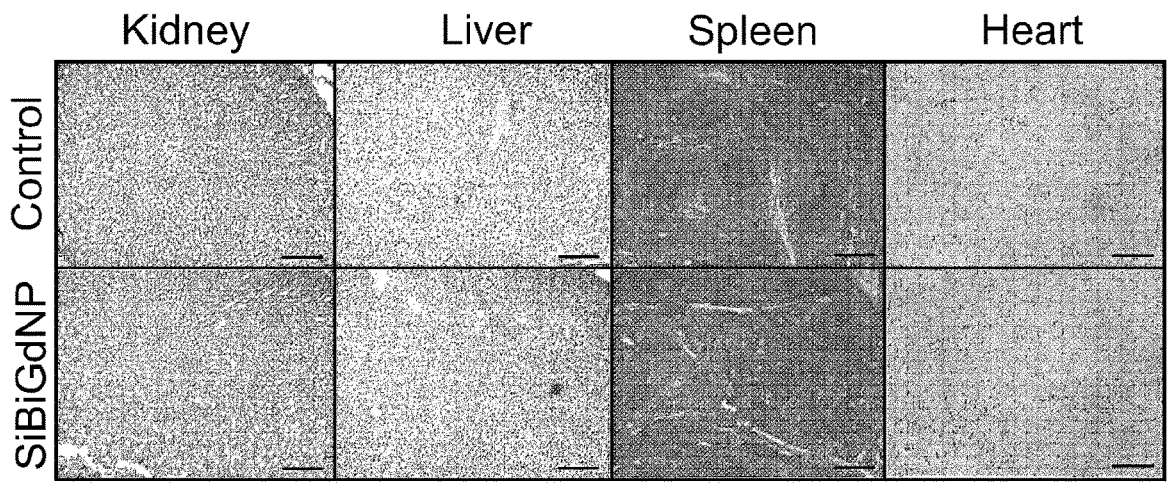
FIG. 9 shows results of H&E staining 24 hours post injection of 0.32 mg/g SiBiGdNP. No difference was observed between the treated and untreated groups. Scale bar=100 µm.

Toxicity measurements were carried out by H&E staining of kidneys, liver, spleen, and heart samples 24 h post-systemic injection, as shown in FIG. 9. The short biological half-life of the nanoparticles restricts contact of the nanoparticles with healthy tissues. Thus, a limited uptake by the reticuloendothelial system was expected (as demonstrated by the H&E staining) and no toxicity was observed.

Example 4. Characterization of SiBiGdNP

Infrared Spectroscopy Measurements

Infrared spectra were then performed with a IRAffinity-1 Shimadzu with a ATR-FTIR (Attenuated Total Reflection Fourrier Transform Infrared) between 550 and 4000 cm$^{-1}$. A solution of SiGdNP-DOTA and SiBiGdNP ([Gd$^{3+}$]=100 mM) at an acidic pH were dried overnight in an oven at 80° C. The spectra were recorded on the obtained powder. The complexation of $Bi^{3+}$ in the nanoparticles generated multiple modifications in the structure (see e.g., Stoia et al, *Anal. Chem.* 1996, 68:3187) the most important of them being the disappearance of the vibration band at 1720 $cm^{-1}$ (C=O vibration band for carboxylic acid) for SiBiGdNP, which confirmed the complexation of Bi atoms in DOTA structure, as shown in FIG. 6A.

Infrared spectra of SiGdNP-DOTA and SiBiGdNP taken under acidic conditions resulted in the following peaks: 1720 $cm^{-1}$: stretching of the C=O of carboxylic acids; 1600 $cm^{-1}$: asymmetrical stretching of the C=O of carboxylates of the C=O of amide and deformation of the N—H of amide; 1440 $cm^{-1}$: deformation of carboxylic acids; 1390 $cm^{-1}$: symmetric stretching of the C=O of carboxylate; 1080 $cm^{-1}$ asymmetrical stretching of the Si—O—Si; 930 $cm^{-1}$: stretching of Si—OH (see e.g., M. Stoia, et al *J. Sol-Gel Sci. Technol.* 2012, 62, 31-40; and B. L. Frey, R. M. Corn, *Anal. Chem.,* 1996, 68, 3187-3193). The vibration band at 1720 $cm^{-1}$ disappeared for SiBiGdNP, which is consistent with nearly all the DOTA being involved in the complexation of Bi (and Gd).

Absorbance Measurements

The complexation of the $Bi^{3+}$ atoms inside the DOTA structure has also been evaluated by absorbance measurements. Several samples containing 200 μM of SiGdNP-DOTA containing from 0 to 100 μM of $Bi^{3+}$ were prepared. Their absorbance spectrum was measured at pH=6 and with a UV-vis spectrophotometer (Varian Cary50). The peak observed at 305 nm corresponds to the complexation of the $Bi^{3+}$ atoms in the DOTA structure, as shown in FIG. 6B.

High Performance Liquid Chromatography

Figure 10:
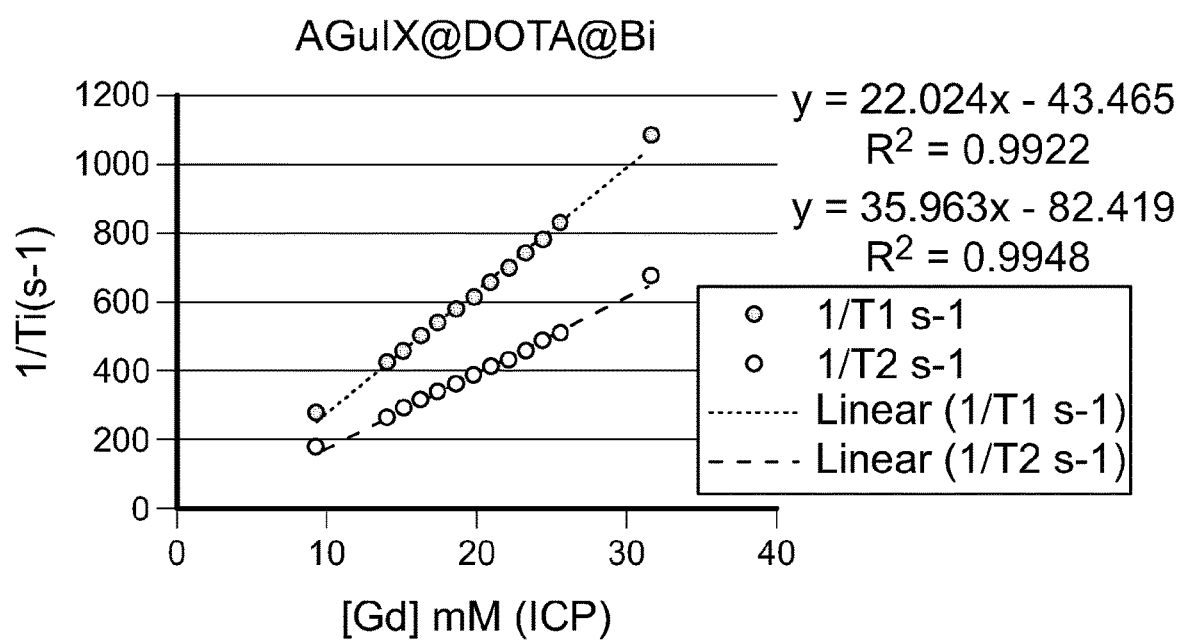
FIG. 10 shows curves of $1/T_1$ and $1/T_2$ at 37° C. under a magnetic field of 1.4 T at different concentration of gadolinium for SiBiGdNp. This experiment leads to $r_1$ of 22.0 $mM^{-1} \cdot s^{-1}$ and $r_2$=36.0 $mM^{-1} \cdot s^{-1}$ for SiBiGdNp.

Gradient HPLC analysis was performed by using a Shimadzu® Prominence series UFLC system with a CBM-20A controller bus module, a LC-20AD liquid chromatograph, a CTO-20A column oven, an SPD-20A UV-visible detector and an RF-20A fluorescence detector. UV-visible absorption was measured at 295 nm for particle characterization or 700 nm for free chelates quantification (UV-visible absorption single wavelength detection). 20 μL of the sample was loaded in the solvent injection ratio: 99% solvent A: 1% solvent C (A=Milli-Q water:TFA 99.9:0.1 v/v; C=$CH_3CN$: TFA 99.90.1 v/v) onto a Jupiter C4 column (150×4.60 mm, 5 μm, 300 Å, Phenomenex®) at a flow rate of 1 mL/min for 7 min. Afterwards, samples were eluted by a gradient developed from 1 to 90% of solvent C for 15 min. The concentration of solvent C was maintained for 7 min. Then, the concentration of solvent C was decreased to 1% for a period of 1 min followed by an additional 8 min at this final concentration to re-equilibrate the system. Before each sample measurement, a baseline was performed following the same conditions by loading Milli-Q water into the injection loop. For measurements, lyophilized particles were first dispersed in water for one hour at room temperature, $[Gd^{3+}]$=100 mM and pH=7.4. Then, particles were diluted to $[Gd^{3+}]$=5 mM and immediately injected for measurement. SiBiGdNP retention time was 12.03 min, a width at half height of 0.62 min and a purity of 97%. The purity was calculated with the absorbance at 295 nm given by HPLC. Results of the HPLC measurements are shown in FIG. 10.

The HPLC spectra presents a main peak around 12-13 min corresponding to the particles. Around 2-4 min, small other peaks are recorded. They correspond to small fragments coming from the hydrolysis of the Si—O—Si bonds from the polysiloxane core. Therefore, these chromatograms reflect the purity of the batches (purity calculated at 295 nm).

The slight change in the retention time can be explained by the change in the surface of the particle (and in the size).

Dynamic Light Scattering

Direct measurements of the hydrodynamic diameter distribution of the nanoparticles were performed via a Zetasizer® Nano S DLS (laser He—Ne 633 nm) from Malvern Instruments. Lyophilized particles were first dispersed in water for one hour at room temperature, $[Gd^{3+}]$=100 mM and pH=7.4. The nanoparticles were diluted to $[Gd^{3+}]$=10 mM and measurements immediately taken. The average hydrodynamic diameter (in number) measured by DLS was 3.9 nm (standard deviation: 0.8) for SiGdNP, 4.1 nm for SiGdNP-DOTA (standard deviation: 0.8) and 4.5 nm for SiBiGdNP (standard deviation: 0.9). The slight increase in size between the particles can come from the increase of size due to the grafting of DOTA-NHS at the surface of the particle and to the purification steps (removal of small particles). It's consistent with the increase in $r_1$ and $r_2$.

Zeta-Potential Measurements

The determination of the zeta-potential of particles were performed with a Zetasizer® Nano S from Malvern Instruments. Prior to taking the measurements, the nanoparticles were dispersed in water for one hour at room temperature, $[Gd^{3+}]$=100 mM and pH=7. Then particles were diluted in an aqueous solution containing 0.01 M NaCl ($[Gd^{3+}]$=5 mM) and measurements were immediately taken. The zeta potential was found to be 1.7 mV for SiGdNP, −7.5 mV for SiGdNP-DOTA and −3.6 mV for SiBiGdNP. The zeta potential evolution was expected. Indeed from SiGdNP to SiGdNP-DOTA, positive charges are "removed" due to amino groups and negative charges are "added" due to carboxylates. The zeta potential at neutral pH decreases. From SiGdNP-DOTA to SiBiGdNP, the zeta potential increased which is consistent with the fact that the complexation of $Bi^{3+}$ leads to a decrease of the overall negative charge.

Quantification of Free Ligand Chelates

Several solutions at a pH of 3 were prepared containing 20 mM of DOTA-NHS and from 0 to 7.5 mM of $Cu^{2+}$. Samples were let for 90 min at 80° C. and were then injected for HPLC analysis (UV-visible absorption was measured at 700 nm). Peak area at 2.9 min corresponding to the DOTA bound $Cu^{2+}$ (i.e., DOTA-$Cu^{2+}$) was determined and the calibration curve equation was found to be:

$$\text{Area (at 2.9 min)}=1616.9\ [\text{DOTA-}Cu^{2+}]-179.47$$

with the concentration in mM and with $R^2$=0.987.

Particles were dispersed in water at a concentration of $[Gd^{3+}]$=100 mM for 1 h at room temperature. Then an excess of $Cu^{2+}$ was added to the nanoparticles solution and the pH adjusted to 3. Samples were let for 90 min at room temperature, diluted if necessary and finally injected without for HPLC analysis (UV-visible absorption was measured at 700 nm). Peak area at approximately 12.5 min, corresponding to the nanoparticles bound to $Cu^{2+}$ was determined and the concentration of free DOTA on the particles determined using the previous calibration curve. The percentage of free DOTA was the ratio between the number of free DOTA and the total number of DOTA. It was 2% for SiGdNP, 47% for SiGdNP-DOTA and 6.5% for SiBiGdNP.

Elemental Characterization

The determination of the accurate concentration of gadolinium and bismuth in the nanoparticle was performed by Inductively Coupled Plasma-Optical Emission Spectroscopy (ICP-OES). The particles were degraded overnight in 5 mL of aqua regia ($HNO_3$ 67% mixed with HCl 37% (1:2; v/v) at 80° C. and at an estimated concentration in gadolinium of 0.01 mM, 0.02 mM or 0.05 mM. Subsequently, the samples were diluted to 50 mL with 0.5 M $HNO_3$ (1:2500, v/v). The ICP-OES was calibrated with a single element standard solution prepared from 1000 ppm Gd-standard and 1000 ppm Bi-standard by successive dilutions with an $HNO_3$ 5% (w/w) matrix. For each particle, the $Gd^{3+}$ and $Bi^{3+}$ composition given is an average of the three samples prepared (0.01 mM, 0.02 mM and 0.05 mM). The massic percentage (i.e., mass percentage or mass percent) obtained is of 8.31 for Gd and 6.1 for Bi in SiBiGdNp.

The determination of Gd, Si, C, N and Bi content of particles was performed by the Filab company (France) by ICP-MS (precision: 0.4%) and are shown in FIG. 1D. For SiGdNP the massic percentage is 13.98 for Gd, 11.45 for Si, 28.95 for C and 8.14 for N. This is consistent with the following average composition for SiGdNP: $(Gd_1 APTES^*_{2.5} TEOS^*_{2.12} DOTAGA^*_{1.02}) \cdot x\ H_2O$. For SiGdNP-DOTA the massic percentage is 8.1 for Gd, 11.3 for Si, 23.48 for C and 7.05 for N. This is consistent with the following average composition for SiGdNP-DOTA: $(Gd_1 APTES^*_{3.4} TEOS^*_{4.3} DOTAGA^*_{1.02} DOTA^*_{0.56}) \cdot x\ H_2O$. For SiBiGdNP the massic percentage is 8.1 for Gd 14 for Si, 23.7 for C, 6.9 for N and 6.1 for Bi. Combining with the massic percentage of Gd obtained by ICP-OES, this is consistent with the following average composition for SiBiGdNP: $(Gd_1 APTES^*_{3.0} TEOS^*_{6.2} DOTAGA^*_1 DOTA_{0.62} Bi_{0.52}) \cdot x\ H_2O$. APTES*, TEOS*, DOTAGA* and DOTA* refer to the corresponding molecules that have reacted and actually present within the nanoparticle.

Stability of SiBiGdNP

Figure 11:
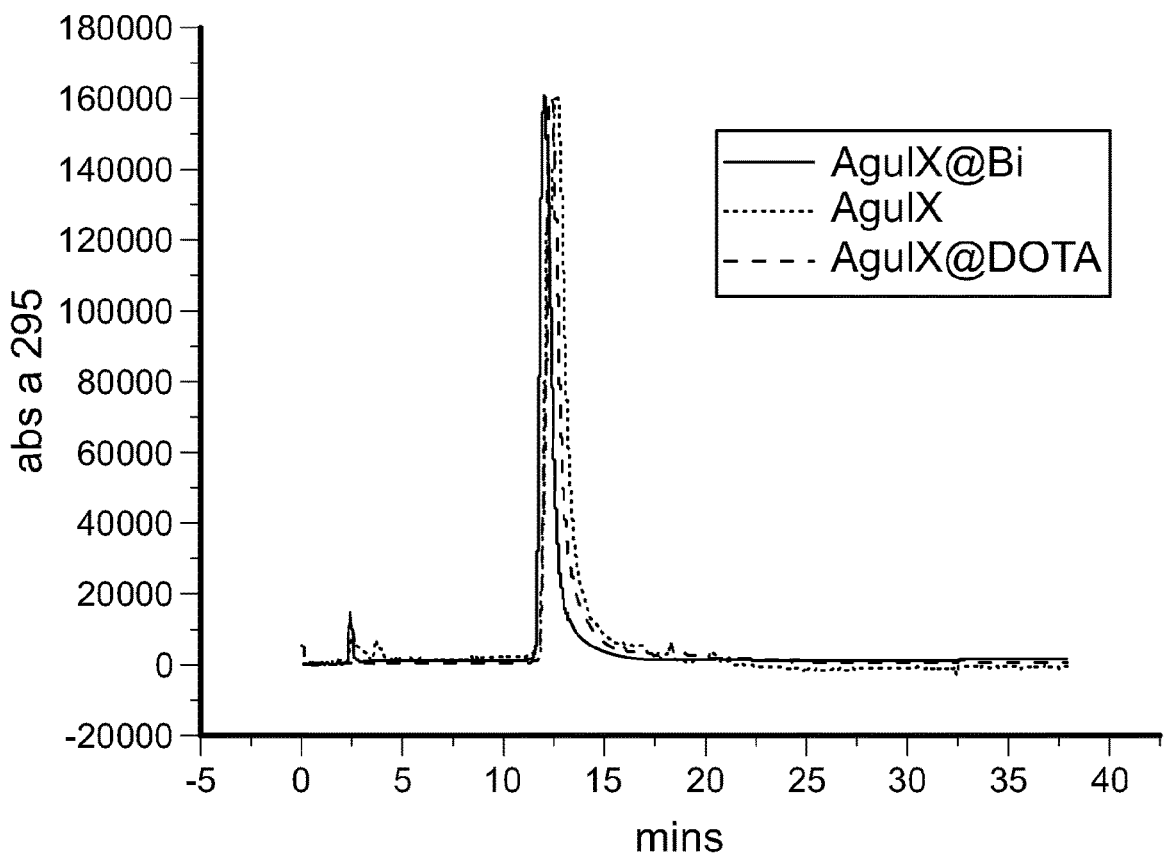
FIG. 11 shows HPLC curves for SiGdNp (i.e., AGuIX), SiGdNp functionalized by DOTA-NHS (i.e., AguiX@DOTA) and SiBiGdNp (i.e., AguiX@Bi). Mean peak around 12-13 min corresponds to the whole nanoparticle. Peaks around 2-4 min corresponds to fragments obtained after hydrolysis of Si—O—Si bonds.

The stability of the nanoparticles was determined by relaxometry measurements over 24 h in aqueous solution with a pH of 5 or 7. SiBiGdNP were dispersed in water at a concentration of $[Gd^{3+}]$=40 mM and the pH adjusted to 7 or 5. The solution was kept at 37° C. for all the experiments. Between 0 and 24 h, the solution was diluted in water and the absorbance spectra recorded using a UV-vis spectrophotometer (Varian Cary50) and the results are shown in FIG. 11.

NMR Measurements

Relaxation time measurements were performed using a Bruker Biospec® operating at a magnetic field of 7 T and at 37° C. Before measurements of $T_1$ (longitudinal relaxation time) and $T_2$ (transverse relaxation time), lyophilized particles were dispersed in water for one hour at room temperature, [Gd]=100 mM and pH=7.4. The SiBiGdNP $r_1$=4.87 $s^{-1} \cdot mM^{-1}$ per $Gd^{3+}$ and $r_2$=3.48 $s^{-1} \cdot mM^{-1}$ per $Gd^{3+}$.

Figure 12:
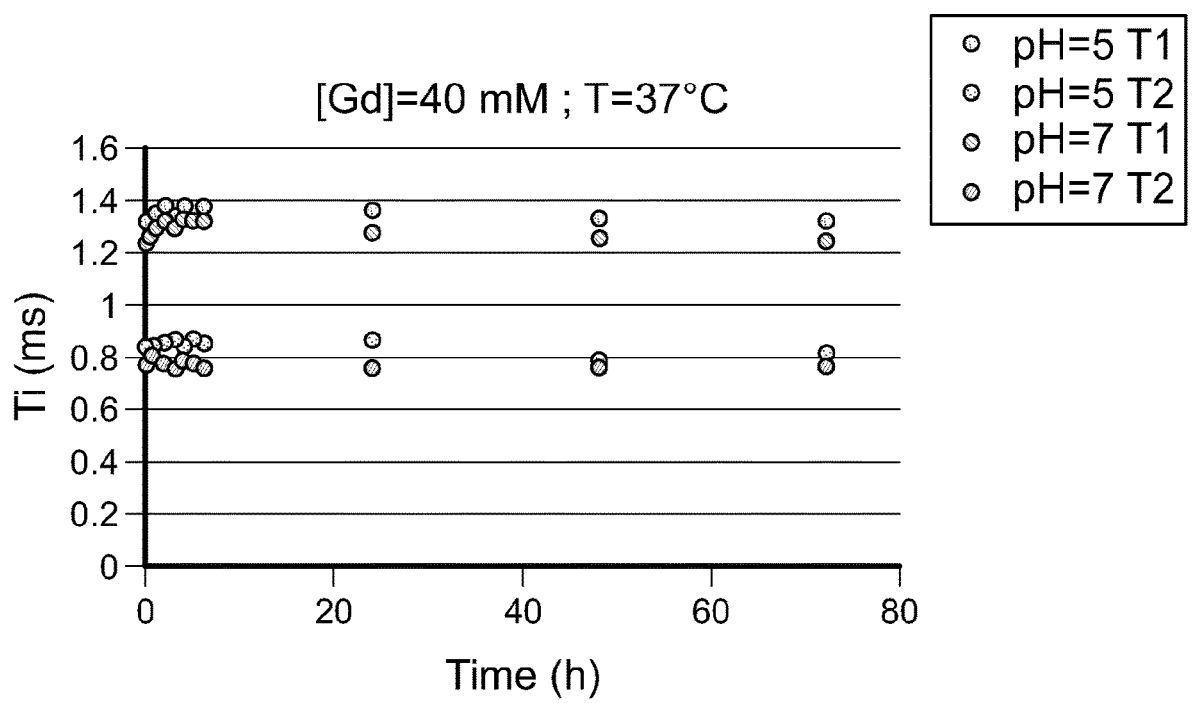
FIG. 12 shows the stability at different pH of SiBiGdNp at 37° C. and a concentration in $[Gd^{3+}]$ of 40 mM. Stability was checked by plotting $T_1$ and $T_2$ (under a magnetic field of 1.4 T) of nanoparticles at pH 5 and 7 versus time. No significant modification was observed for more than 3 days.

Relaxation time measurements were performed using a Bruker Minispec MQ60 NMR analyzer, operating at a magnetic field of 1.4 T and at 37° C. and are shown in FIG. 12. Before measurements of $T_1$ (longitudinal relaxation time) and $T_2$ (transverse relaxation time), lyophilized particles were dispersed in water for one hour at room temperature, [Gd]=100 mM and pH=7.4. For SiGdNP, $r_1$=15.0 $s^{-1} \cdot mM^{-1}$ per $Gd^{3+}$ and $r_2$=21.3 $s^{-1} \cdot mM^{-1}$ per $Gd^{3+}$. For SiGdNP-DOTA, $r_1$=18.0 $s^{-1} \cdot mM^{-1}$ per $Gd^{3+}$ and $r_2$=27.2 $s^{-1} \cdot mM^{-1}$ per $Gd^{3+}$. For SiBiGdNP, $r_1$=22.0 $s^{-1} \cdot mM^{-1}$ per $Gd^{3+}$ and $r_2$=36.0 $s^{-1} \cdot mM^{-1}$ per $Gd^{3+}$. The increase in the $r_1$ an $r_2$ values between the particles can come from the increase of size due to the grafting of DOTA-NHS at the surface of the particle and to the purification steps (removal of small particles). The ratio $r_2/r_1$ is comprise between 1.4 and 1.6. The magnetic properties are expected to be similar for these three particles.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition, comprising:
   a nanoparticle core comprising one or more first linking groups covalently bonded to a first ligand and one or more second linking groups covalently bonded to a second ligand;
   wherein one or more of the first ligands are complexed to $Gd^{3+}$ ions and one or more of the second ligands are complexed to $Bi^{3+}$ ions,
   wherein the nanoparticle core is a silica core or a polysiloxane core,
   wherein the first ligand is selected from 1,4,7,10-tetraazacyclododececane, 1-(glutaric acid)-4,7,10-triacetic acid (DOTAGA) and 1,4,7,10-tetraazacyclododecane-1,4,7, 10-tetraacetic acid (DOTA) and the second ligand is selected from 1,4,7,10-tetraazacyclododececane, 1-(glutaric acid)-4,7,10-triacetic acid (DOTAGA) and 1,4,7,10-tetraazacyclododecane-1,4,7,10-tetraacetic acid (DOTA); and
   wherein the composition comprises a ratio of $Gd^{3+}$ ions: $Bi^{3+}$ ions of from about 1:1 to about 2:1.

2. The composition of claim 1, wherein the one or more first linking groups each comprise a $C_{1-10}$ alkylamine covalently bonded to the first ligand.

3. The composition of claim 1, wherein the one or more second linking groups each comprise a $C_{1-10}$ alkylamine covalently bonded to the second ligand.

4. The composition of claim 1, wherein greater than about 20% of the first ligands are complexed to the $Gd^{3+}$ ions; or greater than about 20% of the second ligands are complexed to the $Bi^{3+}$ ions; or greater than about 20% of the first ligands are complexed to the $Gd^{3+}$ ions and greater than about 20% of the second ligands are complexed to the $Bi^{3+}$ ions.

5. The composition of claim 1, wherein the nanoparticle comprises from about 5 to about 15 $Gd^{3+}$ ions and from about 1 to about 10 $Bi^{3+}$ ions.

6. The composition of claim 1, wherein the hydrodynamic diameter of the nanoparticle is from about 2 nm to about 8 nm.

7. The composition of claim 1, wherein the composition is suitable for intravenous or nasal administration.

8. The composition of claim 1, wherein the first ligand 1,4,7,10-tetraazacyclododecane-1,4,7,10-tetraacetic acid (DOTA) and the second ligand is 1,4,7,10-tetraazacyclodecane-1,4,7,10-tetraacetic acid (DOTA).

9. The composition of claim 1, wherein the first ligand is 1,4,7,10-tetraazacyclododececane, 1-(glutaric acid)-4,7,10-triacetic acid (DOTAGA and the second ligand is 1,4,7,10-tetraazacyclododececane, 1-(glutaric acid)-4,7,10-triacetic acid (DOTAGA).

* * * * *

UNITED STATES PATENT AND TRADEMARK OFFICE
CERTIFICATE OF CORRECTION

PATENT NO. : 11,590,225 B2
APPLICATION NO. : 16/467698
DATED : February 28, 2023
INVENTOR(S) : Ross Berbeco et al.

It is certified that error appears in the above-identified patent and that said Letters Patent is hereby corrected as shown below:

On the Title Page

Column 1 item (72) (Inventors), Line 3, delete "Lyons (FR);" and insert -- Lyon (FR); --

In the Claims

In Column 30, Lines 24-25, Claim 1, delete "10-tetraazacyclododececane," and insert -- 10-tetraazacyclododecane --

In Column 30, Line 28, Claim 1, delete "10-tetraazacyclododececane," and insert -- 10-tetraazacyclododecane, --

In Column 30, Line 57, Claim 9, delete "10-tetraazacyclododececane," and insert -- 10-tetraazacyclododecane, --

In Column 30, Line 58, Claim 9, delete "(DOTAGA" and insert -- (DOTAGA) --

In Column 30, Lines 58-59, Claim 9, delete "10-tetraazacyclododececane," and insert -- 10-tetraazacyclododecane, --

Signed and Sealed this
Sixteenth Day of May, 2023

Katherine Kelly Vidal
*Director of the United States Patent and Trademark Office*